United States Patent
Johnson et al.

(10) Patent No.: US 11,819,436 B2
(45) Date of Patent: Nov. 21, 2023

(54) UNLOADING KNEE BRACE APPARATUS WITH CONFORMING AND DISTRACTING HINGE

(71) Applicant: Icarus Medical, LLC, Charlottesville, VA (US)

(72) Inventors: David T. Johnson, Charlottesville, VA (US); Evan Eckersley, Charlottesville, VA (US); Emily Hubbard, Purcellville, VA (US); Ben Scire, Hopkinton, MA (US); Isaiah Woo, Williamsburg, VA (US); Collin Farill, Charlottesville, VA (US); Carter Kitchin, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 17/211,635

(22) Filed: Mar. 24, 2021

(65) Prior Publication Data

US 2021/0205111 A1    Jul. 8, 2021

Related U.S. Application Data

(60) Continuation of application No. 17/074,542, filed on Oct. 19, 2020, now Pat. No. 11,564,824, which is a
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 5/0123; A61F 5/0102; A61F 2005/0179; A61F 2005/0137; A61F 2005/0167; A61F 2005/0158; A61F 2005/0169; A61F 5/013; A61F 2005/0155;
(Continued)

(56) References Cited

U.S. PATENT DOCUMENTS 5,908,398 A * 6/1999 DeToro ................ A61F 5/0111
                                                      602/27
6,527,733 B1   3/2003 Ceriani et al.
(Continued)

OTHER PUBLICATIONS

Application No. PCT/US 22/21822, International Search Report and Written Opinion dated Aug. 3, 2022.

*Primary Examiner* — Ophelia A Hawthorne
(74) *Attorney, Agent, or Firm* — Woods Rogers Vandeventer Black PLC; Nathan A. Evans

(57) ABSTRACT

An adjustable tension knee brace for unloading weight from a knee joint afflicted with osteoarthritis, thus reducing pain and improving mobility, comprising: an upper and lower frame connected by an unloading hinge assembly, optionally comprising a sensor and processor allowing for remote or automatic control of brace tension. In embodiments, the brace includes a user mechanism that is capable of adjusting a tensioning element while the brace is being worn. In other embodiments, electronic motors, sensors, and indicators may be included in the brace to improve brace performance and user interaction.

21 Claims, 8 Drawing Sheets

Related U.S. Application Data division of application No. 15/585,968, filed on May 3, 2017, now Pat. No. 10,806,619, application No. 17/211,635 is a continuation of application No. 17/074,571, filed on Oct. 19, 2020, which is a continuation-in-part of application No. 15/585,968, filed on May 3, 2017, now Pat. No. 10,806,619.

(60) Provisional application No. 62/331,315, filed on May 3, 2016.

(58) Field of Classification Search
CPC ...... A61F 2005/0132; A61F 2005/0144; A61F 2005/0148; A61F 5/01; A61F 2005/0134; A61F 5/0111; A61F 2005/0141; A61F 2005/0146; A61F 2005/0197; A61F 2220/0008; A61F 5/02; A61F 5/0585; A61F 2002/6818; A61F 2002/701; A61F 2002/7645; A61F 5/00; A61F 5/0113; A61F 5/028; A61F 5/055; A61F 2002/5072; A61F 2002/6854; A61F 2002/7635; A61F 2/604; A61F 2/64; A61F 5/05858
See application file for complete search history.

(56) References Cited

U.S. PATENT DOCUMENTS

| | | | |
|---|---|---|---|
| 7,608,051 B1* | 10/2009 | Nace | A61F 5/0123 602/1 |
| 2005/0177082 A1* | 8/2005 | Bledsoe | A61F 5/0123 602/26 |
| 2007/0055190 A1* | 3/2007 | Bonutti | A61H 1/02 601/5 |
| 2015/0119777 A1 | 4/2015 | Garrish | |
| 2015/0173927 A1 | 6/2015 | Castillo | |
| 2021/0030577 A1 | 2/2021 | Johnson | |

* cited by examiner

UNLOADING KNEE BRACE APPARATUS WITH CONFORMING AND DISTRACTING HINGE

CROSS-REFERENCE TO RELATED APPLICATIONS

The present application is a continuation of and relies on the disclosures of and claims priority to and the benefit of the filing dates of U.S. patent application Ser. Nos. 17/074,571 and 17/074,542, filed Oct. 19, 2020, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. This application also relates to and relies on the disclosures of and claims priority to and the benefit of the filing date of PCT/US2020/047904, filed Aug. 26, 2020. The disclosures of those applications are hereby incorporated by reference herein in their entirety.

FIELD OF THE INVENTION

The present invention disclosed herein relates generally to orthosis knee braces to relieve pain and discomfort by unloading the joint by redistributing the weight on the knee joint to other parts of the body and/or providing assistance in extension of the joint.

BACKGROUND OF THE INVENTION

Osteoarthritis (OA) is a degenerative joint disease characterized by chronic inflammation, breakdown, and eventual loss of the joint cartilage, causing deterioration of the underlying bone. The patellofemoral compartment, in particular, is one of the most frequent points of knee pain experienced by those with OA. While unloading braces have been used as inexpensive therapeutic solutions for knee OA, they have been overwhelmingly ineffective in preventing and reducing joint pain. The various embodiments of the present invention aim to design a knee brace that unloads the knee joint and reduces pain on a knee joint impaired by OA. The orthoses described herein are, among other things, focused on the transfer for forces away from an injured region of the knee, or unloading weight from the anterior region of the knee for patients suffering from patellofemoral pain (PFP) or patellofemoral arthritis.

Arthritis is currently the most common cause of disability among adults in the United States. More than one hundred different rheumatic conditions fall under arthritis, the most common of which is osteoarthritis (OA), a degenerative joint disease marked by a chronic deterioration of joint cartilage and the underlying bone. OA is one of the most common joint disorders in the United States, and the number of those afflicted is only projected to increase in the midst of an aging population and increasing levels of obesity. Twenty-seven million adults in the U.S. alone are affected by the disease. As the most typical type of arthritis, the disorder has commonly affected the knee, and the patellofemoral (PF) compartment within the knee joint in particular has been one of the most frequent points of knee pain in the outpatient setting. The PF compartment performs a key role in daily movement and activity, enabling mobility over a large range of motion through flexion, extension, and rotation of its associated components. One of the most non-invasive and widely accepted methods for prevention of further deterioration of the articular cartilage within the knee joint is by using a knee brace. The joint itself, including its underlying cartilage, can only support a certain amount of force before the cartilage begins to wear away, and unloading knee braces decrease the amount of force on the joint.

According to the American Academy of Orthopedic Surgeons and the U.S. Center for Disease Control and Prevention, nearly half of Americans develop symptoms due to knee OA by the age of 85, and the incidence rate for PF pain syndrome has been reported to be approximately 22 adults for every 1000 adults per year. In addition, up to 10 percent of the U.S. population suffers from pain and loss of function from patella arthritis and cartilage wear. The high prevalence of these injuries suggests that the condition affects a significantly large portion of the adult population and will have a growing impact on healthcare systems in the future. On average, total knee arthroplasty, or knee replacement surgery, costs between $10,000 and $30,000, and over 600,000 surgeries are performed each year. Other surgical procedures such as articular cartilage restoration, osteotomy, and unicompartmental knee replacement, as well as corticosteroid and hyaluronic acid injections to reduce inflammation and absorb shock, respectively, are also very expensive. Thus, preventative treatments that reduce the amount of stress, pressure, and invasive procedures on the knee are necessary for improving the quality of life for patients and for reducing potential medical costs.

In addition, robust braces enable those with severe joint injuries to remain active when joint replacement is not appropriate. It is estimated that 27 million adults in the U.S. are suffering from osteoarthritis, and 454,652 patients with severe joint injuries and arthritis received knee replacement surgeries in 2004. Currently, nonpharmacological approaches, such as physical therapy, and pharmacological methods are primarily used to treat knee OA. When these are proven to be ineffective, the treatment method culminates to surgery, and drawbacks involve internal joint bleeding, bone healing failure, nerve or tissue damage, and infection. Thus, the development of a knee brace that significantly unloads force on afflicted joints, prevents pain and disability, and does not require many other treatments in conjunction is necessary to address the challenges associated with establishing a purely non-pharmacological, orthotic approach to treating knee OA. The main aim of the various embodiments of the present disclosure is to develop a knee brace that significantly unloads force from the patellofemoral compartment of a knee joint afflicted with osteoarthritis in order to relieve pain and disability.

Other conditions such as knee flexion contracture (KFC), quadriceps weakness, and neurological conditions that impact proper muscle and joint function, are also lacking in treatment options. A brace that can transfer forces away from the knee joint and quadriceps has promise to uniquely benefit patients who may suffer from these conditions. Transferring forces away from the joint may also allow the patient to delay or prevent surgical procedures such as a joint replacement.

OA Knee Braces

Osteoarthritic knee braces primarily comprise a rigid, or semi-rigid, frame with an upper frame member called an "upper cuff" situated across the anterior thigh, and a "lower cuff" across the anterior or posterior tibia; and, straps are on the opposing side of the cuffs to secure the frame onto the user's leg. The upper and lower cuffs are connected by a rotary hinge assembly that pivots through a user's normal range of motion, or less depending on the injury.

In OA, the disease process includes degradative enzymes that erode the articular cartridge, leading to bone-on-bone contact, which is the primary source of the user's knee pain. OA knee braces classified as "unloading" braces pull the femur and tibia apart so that there is not bone-on-bone contact when the user is load bearing, such as walking, standing, exercising, etc. This is accomplished by the brace lifting the femur, and/or pulling down the tibia, or otherwise keeping the femur and tibia condyles from making direct contact through the actions of the upper and lower cuffs locking the femur and tibia in positions relative to the other.

Unloading knee braces may also comprise hinge assemblies that exert a force in the medial to lateral direction to push the knee joint inward, thus separating the femur and tibia condyles. For example, there may be one hinge assembly in the brace, such as for a brace to treat OA in the left medial compartment with a hinge assembly on the medial side of the knee joint; or hinge assemblies on both sides. The hinge assembly may comprise a component (e.g. an inflatable pad) that pushes the knee joint laterally, e.g. inward and/or apart, to unload forces on the medial side of the knee, and thus reduce the user's pain.

The hinges in unloading knee braces may also comprise components similar to a built-in breaking system where the user experiences an increase in tension as the knee is bent to prevent the user's knee from collapsing while bending. The hinge assembly and cuffs engage in a majority of the work that the leg muscles would otherwise do to stabilize the knee joint through its entire range of motion.

More recently, a number of OA knee braces have been marketed to consumers who wish to maintain an active life-style in spite of their medical condition. OA knee braces are now available that comprise hinge assemblies with the ability to exert forces to assist the user in movement, otherwise known as "swing assistance" or "knee extension assistance". The hinge's exerted restoring forces can be counter to the user's original direction of movement, such as propelling the user's knee from a flexed to an extended position after the user has bent down. The hinge assemblies primarily comprise springs and/or elastic members (tensioning elements) that store potential energy when the user is bending their leg, such as crouching down, during which the elastic members are stretched, or the springs members are compressed or stretched. The restoring force generated from the compression or stretching is used to assist the user when they move to extend their leg.

What is needed within the OA knee brace industry, though, is a knee brace that effectively both unloads the user's weight off the knee joint while dampening downward forces and generating restorative resistance forces that provide stability and support to weakened muscles. It would also be beneficial if the knee brace provides knee extension assistance to the active user. There is also a need for an improved mechanism of unloading that does not require pushing the knee inward, but instead relies upon a well-fitting rigid or semi-rigid frame and straps, and/or hinge assemblies that are of an adjustable tension that can be activated by the user as needed, and of significantly higher tension levels than the prior art's to engage in the mechanical work that is normally done by the muscles of the knee while pulling the femoral and tibia condyles apart.

SUMMARY OF THE INVENTION

Various embodiments of the present disclosure comprise a novel type of unloading knee brace that has been designed to reduce the amount of pain that patients experience as a result of PFP or knee joint OA. The knee braces and hinge assemblies disclosed herein work by using one or a combination of the following mechanisms:

a. generating a force or forces opposing the bending or contracting/flexion of the knee joint,
b. applying a force or forces to the sides of the leg that result in unloading one or more compartments of the knee,
c. hinges that distract forces from one or both sides of the knee in the tibiofemoral compartments, and/or
d. hinges that are curved that conform to the shape of the users knee.

The braces described herein are suitable for a knee joint, an elbow joint, an ankle joint, a shoulder joint, a hip joint, or a wrist joint; while application of this technology for the knee joint will be presented here in detail, one of ordinary skill in the art could readily apply this disclosure and teachings herein to an elbow, hip, shoulder, ankle or a wrist brace. The brace effectively unloads a significant amount of force within the knee by using a low- to high-tension resistance mechanism described herein, and by distributing the force to other areas of the body. This results in reduced contact pressure in areas of the knee afflicted with OA, and therefore less pain. Other braces are described that have different mechanisms of unloading or distracting pressure in joints as well.

Some embodiments described herein allow the user to: quickly (e.g., in aspect from about 1-5 seconds, for example) engage and disengage tension in each joint mechanism as needed, including in aspects while the brace is being worn; adjust the amount of tension, including while the brace is being worn and without the need for a medical professional's assistance; allow for tension to increase with increasing degrees of flexion; and limit the range of extension and flexion in the joint. The device is particularly suitable for people afflicted with patellofemoral osteoarthritis (OA), cartilage damage, meniscus damage, knee stability issues, and other types of knee conditions for which pain intensifies during the bending or contracting of the knee, and for patients who lack the strength (e.g., quadriceps weakness) to extend their knees either during exercise or simple life functions, such as standing from a seated position. The various embodiments of the brace and hinge assemblies disclosed herein provide enhanced support for stabilizing the knee joint, and they can enhance the user's physical performance by providing extension assistance. Another version of the brace may have the tensioning elements oriented such that the brace resists extension and assists with flexion. The tensioning mechanism may be used with or without the device. This type of device can treat knee flexion contracture, which may be used to help patients recovering from joint replacement surgery improve range of motion.

The various embodiments of the brace and hinge assemblies disclosed herein may also be applied to other orthotics designed to treat other human joint, such as elbows, shoulders, ankles, wrists, and hips, wherein a support in one part of the joint is operatively connected to another part of the joint via a variety of the tensioning mechanisms described below that may alter the amount of force between parts of the joint. For example, a shoulder brace may apply a posteriorly directed force through the shoulder to unload the anterior direction, or other direction(s), to alleviate pain. In this example, part of the shoulder brace will attach to the injured part of the body and will anchor to another part of the body, such as the shoulder opposite to the injured shoulder. Rigid and semi-rigid parts may be used in conjunction with the tensioning mechanism to create the desired force environment for the joint.

Unloading Brace Vertical Support

The various embodiments of the present disclosure comprise a knee brace that effectively unloads the user's weight off the knee joint via a rigid or semi-rigid vertical support that, in aspects, partially or completely connects to the user's femur and tibia, and with a pivoting hinge assembly connecting an upper and lower portion of the vertical support. In some embodiments, the posterior side of the vertical support comprises one to three straps on the upper and on the lower portion, or other mechanisms to connect the device to the knee, or elbow, or ankle, by way of example, which may be oriented in a variety of ways relative to the vertical support.

It is noted that the vertical support of the present disclosure may also be used with a wide variety of types of hinge assemblies previously known in the art for use by knee patients in order to effectively unload weight from the knee joint. One such assembly may be the combination of rigid and semi-rigid materials that enable the brace to be connected to or contained within an elastic sleeve or support that partially or fully encompasses the joint.

The various embodiments of the knee brace comprise a vertical support with an upper frame and a lower frame that are connected via a hinge assembly on one side (for a medial or lateral brace), or via two hinge assemblies (for a full brace). Furthermore, in embodiments, the vertical support comprises an arcuate, curved, semi-circular rigid or semi-rigid unit situated above and below the knee, and connected via a geared or ungeared, pivoting hinge assembly, in examples. The upper and lower frames may further comprise at least one strap or other connection mechanism to secure the brace to the user's leg; and the upper portion may have straps and/or a material for supporting the back of the thigh to effectively distribute force away from the knee. The upper and lower portions may also be secured with a hook and loop type material, or a clip-type fastener or similar method.

The brace can be one-sided or bilateral (as in a right and left, or medial and lateral support), the determination of which is based on whether the knee is injured medially or laterally, or in the femoral compartment, which is approximately central. The tensioned brace hinge assembly should be proximal to the injured part of the knee. A user benefiting from a high-tension brace would ideally use a brace with both lateral and medial side supports to generate torque on both sides.

The amount of torque can be modified by the strength and number of elastic materials, and the amount of torque may vary on each side to address the user's specific OA condition. The brace frames disclosed herein are capable of targeting damage to the patellofemoral compartment; but other types of knee injuries and medical conditions may benefit from only a side support vertical member and/or one hinge assembly.

The brace can also accommodate a patient who experiences more symptoms of OA in one compartment of the knee than the others, by applying a force on the opposing side of the unicompartmental OA present in the patient's knee. This can be achieved by a variety of methods known to the art; for example, the condylar pad on one side of the joint may be stiffer or thicker than the condylar pad on the other side of the joint. The use of shims that can be connected to the side plate or hinge capsule and adjusted based on the degree of varus/valgus present in the user's knee may also apply.

Another application of the brace may involve using the same tensioning mechanisms taught herein to assist flexion instead of opposing flexion. This could be accomplished by changing the location of the tensioning element such that it is located on the posterior side of the hinge assembly and encourages flexion of the joint by maintaining tension in the tensioning element. This application of the device would be useful for those recovering from an injury or undergoing physical therapy, as an indication of knee health after recovery is the range of motion (flexion) the knee can achieve as swelling decreases in the joint.

The brace can be partially or fully automatically designed by software that generates a design based on a 3D scan consisting of cloud point data, accompanied by information on the user such as the severity of their injury, information on the misalignment based on radiographic measurements, measurements extrapolated from 3D scans, and other user biometric data such as height, weight, and age, or any combination of this information. The model developed can also use this information to develop implantable devices within the joint to improve joint function. These may also be used to serve as a substrate for cartilage growth on the implant or to shape how cartilage grows in the joint in a desired way. The implant may also be placed to assist cartilage growth in another area that is near or related to the implant. Artificial intelligence or machine learning can be used with or without finite element analysis to determine the shape of an effective or assistive implant, and AI, machine learning, and FEA, or combinations thereof may consider all of the input data above to improve overall body mechanics. This approach may be applied to more than just the knee, but also the ankle and hip, and how these joints relate to each other to improve body function. This can also be applied to the shoulder, elbow, wrist, back, and neck joints, or combinations thereof.

Brace Materials: In embodiments, the vertical support is made from rigid and/or semi-rigid plastic, metal, other lightweight materials, such as carbon fiber or another suitable material that are mostly inelastic yet flexible, and thus distribute weight-load knee forces. 3D printing with common thermoplastics are ideal materials for fabricating the brace described herein.

Because the knee braces are subjected to high tension or high torque from the hinge assembly, tight, form-fitting contact with the body is preferred. The brace may further comprise light padding lining the upper and lower portions, and/or the straps or other connection mechanisms. In aspects, the fit and material composition are designed to provide a coefficient of friction between the brace and a user's leg so as to increase adhesion to the user's leg, and thus facilitate the transfer of weight-load forces off the knee joint, while remaining comfortable to wear. The upper and lower portions and/or straps or other connection mechanisms can be contained or built within an elastic sleeve to reduce the friction coefficient at the body/brace interface. The fabrication method combined with using strong and lightweight materials will facilitate this design feature. Furthermore, the brace can be made from common materials, such as braided tensioning elements, where applicable, and may therefore be less expensive and more accessible to users that may not normally be able to afford a performance brace. 3D-printed versions of the brace frame may have padding that is 3D printed continuously or separately attached. 3D printed padding comprises a compressible matrix that conforms to the body and provides cushion.

In aspects, the brace frame, or vertical support, comprises: an upper rigid, or semi-rigid, frame, sized to fit a user's femur adjacent to and above a user's knee joint, and a lower rigid, or semi-rigid, frame, sized to fit a user's tibia adjacent to and below the user's knee joint.

Size: The knee brace can be custom made for the user based on one or more of: size, weight, level of physical activity of the user; weight and flexibility of the brace; etc. Or it can be sold over-the-counter based on size (for example, small, medium or large), and/or by level of tension (low/medium/high). Or, the brace may be custom made to fit a particular user using digital imaging. In a preferred embodiment, the brace is form-fitting to the knee joint, lower femur, and top tibia, in order to redistribute the load off of the knee joint, when the device is being used to unload forces. The brace may conform to digital images or a three-dimensional scan and this fitting process may be automated or partially automated. Software can orient the leg in the proper direction and scale the leg and brace properly.

Hinge Assemblies

In embodiments, the present invention comprises at least one tensioning element (e.g., a tensioning element, an elastic band, or a spring) of low, moderate, or high tension, two intermeshed, teethed gears rotating in unison as the user flexes and extends the knee joint, and a method of controlling the degree of extension and flexion the joint can achieve while the user is wearing the brace. Other embodiments do not require teethed gears but instead are toothless with curved adjacent parts that glide on each other and are made from a low-friction material, in aspects.

Hinge assemblies can be used with the unloading brace vertical support disclosed herein; and/or with other knee braces or joint braces known in the art.

In the hinge assemblies disclosed herein, the amount of tension for unloading can be adjusted by, for example: adding more tensioning elements of the same or of different levels of tension; adding more tensioning elements of the same or of different levels of diameter; and/or by substituting tensioning elements with different elastic properties (e.g., stiffer bands or springs to create more tension; and/or by moving a hinge component to fix one end and/or the center of a tensioning element to prevent it from further extension, thus increasing the tension in the element (e.g., see embodiments 2-4 of the hinge assembly, infra)). The hinge assembly may include smoothed sections to prevent damage to the tensioning element(s), and to allow for drawing-stretching-extending the tensioning element over the hinge, whether or not the tensioning element(s) come into contact with the rotating gears.

When more than one tensioning element is used, the tensioning elements may be located, in certain aspects, adjacent longitudinally in the anterior side of the hinge assembly, and/or the posterior side, such as in parallel, or one atop the other, such as in series. Another design feature, in aspects, is that a plurality of tensioning elements improve safety of the brace by providing a backup support in the unlikely event that a band breaks or detaches.

If a tensioning element is to be used, in embodiments, hinges with bands as large as ¾ inch and as little as ⅛ inch in diameter are envisioned, and larger and smaller bands could be used in the same brace.

Tensioning elements having different levels of tension comprise materials, in examples, such as: real rubber, braided synthetic rubber cords, exotic elastic or other elastic materials. Braided bands offer protection to the elastic material, and other bands can use thin protective sheaths or a wet or dry lubricant to allow for smooth drawing over the hinge, in aspects. Bands that are 3D-printed with many individual elastic strands oriented in the direction of tension will make a preferred tensioning element.

An additional hinge assembly may be envisioned that is comparative to the gliding and rolling of the knee joint. This version may involve a slot that allows for the gliding and rolling motion of the knee wherein the slot is a pin in the upper and or lower frame. A tensioning element may be anchored between the upper and lower frames to slow or to impede the forward movement of the knee joint, in a way that best matches the natural movement of the knee.

Single-Upright Mechanism:

Extension-Flexion Stops: In addition to a controllable tensioning mechanism as described in embodiments 1-5, for example, extension-flexion stops may be used to prevent users from hyperextending or hyperflexing joints that may already be prone to injury, as well as simply limiting the degree of flexion or extension. In disclosed hinge assemblies herein, the brace hinge may comprise various methods of controlling the degree of extension and flexion of the joint. In one inventive embodiment, a slot that is radially oriented to the pivoting point of the hinge can be cut out of the hinge or created during fabrication of the joint. In other words, the hinge may comprise a slot, for example a slot that is radially-oriented to the pivoting point of the hinge. The degree of flexion and extension that the angle between the two frames of the brace can achieve during an articulated joint movement can be controlled by placing premade inserts at chosen locations in the radially oriented slot. The premade inserts can be fabricated with the material strength and shape to withstand articulated and intense joint movements without fracturing, bending, or slipping out of the slot. Either the side plates or hinge capsules will help secure the inserts into the hinge, without restricting smooth motion of the hinges/intermeshed teethed gears. This slot and inserts at various points in the brace allow for user customization of degree of flexion and extension allowed by the device at the hinge point.

Another variation of the extension-flexion stops is through a fabricating process, wherein inserts that may be placed in between the anterior and/or posterior of the upper and lower frame hinges can be used to control the degrees of flexion and extension in the joint at, for example, the hinge point. For example, the insert may be placed on the anterior side of the frame hinge between the gears in order to limit the degree of extension of the joint; alternatively, the inserts may be placed on the posterior side of the hinge to limit the degree of flexion of the joint.

The geometry of the teethed gears and hinge(s) may also be altered upon fabrication of the hinge grouping in order to limit the degrees of extension and flexion the joint can perform during use of the brace or a limit on the degrees of flexion and extension allowed by a hinge point on the device. For example, the geometry of one gear can be designed such that it does not fit within the opposing intermeshing gear at a certain degree of flexion or extension. The teethed gears/hinge preferably comprise a durable material that can resist the tendency for movement during extension or flexion of the joint.

Tubes: In another embodiment, the hinge assemblies comprise a tube or tubes through the geared components in the brace, and/or the brace frame, and comprise a tube or tubes within the support structure. The tubes may be integrated partially or completely within the frame, or may be external to the frame. The tube(s) in the brace components may be balanced to offer sufficient strength while minimizing the bulk and weight of the component. Materials can be chosen to allow for smaller or larger sized brace components. The tubes may be located anywhere within the frame of the brace and may orient the bands in a plurality of ways depending on a user's need, treatment, preference, comfort, injury, performance requirement, etc.

Tensioning elements can be located at different positions within the brace—above and/or below the hinge, and the hinge can draw lace or wire over the hinge causing the tensioning elements to elongate. The tension in the system would be modulated in a similar way, and the tension adjustment mechanism can be placed at various locations on the brace.

Another feature includes using tensioning elements that have a distinct ending point that limits the degree of flexion based on the length of the tensioning element and the length of the component, by limiting the amount of band drawn over a section of the hinge that acts as a cam, which generates a mechanical advantage as it draws the tensioning element(s) apart from its anchored ends. For example, in embodiment one, the bands are fixed at both ends; in embodiment two and four, infra, for example, the band(s) are fixed at the distal end only and tension is adjustable at the proximal end; and in embodiment three, infra, the band(s) are fixed at both ends, but are adjustable for tension. The shape of the cam can be modified to increase or decrease the elongation of on the tensioning element and therefore affect the torque generated.

The tension, or counter-force, in the hinge assembly may be adjusted bye increasing the number of tensioning elements to increase the tension, and/or by using tensioning elements of more stiffness for a higher tension. In an embodiment, the knee brace is manufactured for a specific tension (low, medium, and high). In another embodiment (e.g., the second through fifth hinge embodiment, infra), the tension is adjustable by deactivating a hinge mechanism to allow the tensioning element(s) to stretch, or by activating the mechanism to block the tensioning element from stretching on one or both ends, thus increasing the tension in the band(s).

In another embodiment, comprising multiple bands, the elements can be mixed or combined with different strengths and sizes based on the user's preferences or needs, and the different elements can be engaged at different degrees of flexion. For example, one band could be engaged from 5-20 degrees of flexion, by way of example only, at which point another band would engage to increase the resistance.

The bands can be secured through a number of methods, including the use of clamps or pins or anchors through the tensioning element or through which the tensioning element may be engaged, and hole(s) in the brace may comprise components to prevent the band ends from slipping out of hole(s) while the brace is under tension. Other band geometries can be used, such as circular bands that hook into the top and bottom components of the brace.

The distal and proximal hinge are preferentially fabricated as a continuous material with the vertical supports, or alternatively are secured to the brace frame by bolts, rivets, pins, screws or another similar attachment mechanism. A brace support may be of plastic or carbon fiber and could be shaped to include the tensioning element supports and the gearing mechanism. An unloading brace can be made through any a combination of 3D printing, injection molding, water-jetting, casting, extruding, pultruding, or other similar ways. This brace can use multiple injection-molded components that connect together and house tubes, tensioning elements, and/or wires on, or partially or completely within, the components. These components may be connected to metal frame parts that generally shape around the leg or other limb. This version of the brace may be an alternate version of the 3D-printed version as a lower-cost or higher-volume production alternative.

The hinge components on the lateral and/or medial side of the knee can be spaced snugly to keep a narrow profile. If multiple elastic materials are drawn across the hinge, they can be oriented vertically or horizontally to the desired dimensions and/or tension of the brace. The components can be symmetric or shaped to contour the leg.

The hinge that connects the top and bottom components of the brace can, in aspects, be a U-shaped joint or another component that will offer lateral stability to the brace. These can be threaded or designed in a way to minimize the size and profile, such as using E-clips (circlips) or pressing the components in place.

Additional Applications

The hinge and tensioning assemblies described herein may be applied to other human joints, including but not limited to the ankle, shoulder, hip, elbow, and wrist joints. These embodiments of the present invention may include a support of one part of the joint being operatively connected to a support of another part of the same joint. This connection may comprise a tensioning element, which may or may not be adjustable, so that the brace may apply force in a direction favorable for rehabilitation or support of a joint.

For example, in an embodiment, an ankle brace may comprise an ankle cuff and a lower portion that connects to a region or regions of the foot. The ankle cuff may be connected to the lower portion of the ankle brace by one or more materials and/or adjustable tensioning elements that will apply force to desirable locations of the ankle and foot in order to provide the ankle with more support.

In another embodiment, the brace may comprise a portion that can be secured on one end to the hip of a user and to the leg of the user of the other end. By connecting these two ends of the brace with a tensioning element, the ball and socket joint of the hip may be adjusted to better align the femur and pelvis in a way that is physically preferable for the patient.

Any additional embodiments of this brace, as they are applied to other joints, may employ a variety of optionally adjustable tensioning elements, such as combinations of tensioning elements in series or parallel, and the strength of the tensioning elements may be adjusted depending on the type of joint and treatment needed per user. These additional embodiments may also employ the adjustable tensioning mechanisms, infra, in order to allow for dynamic use of the brace.

Tension Adjustment and Engage/Disengage Features

Another feature of the brace design taught herein is that in embodiments two through five, infra, the user can either fully or partially disengage the tension mechanism. The tension engagement-disengagement feature allows the user to increase the tension in the hinge assembly to provide more stability and off-loading of their weight from their knee, such as when climbing stairs, and then to turn off the mechanism or decrease tension when it is no longer needed, such as at the top of the stairs, so that the user can more easily walk or jog with a fuller range of motion. The current invention allows for this adjustment in real-time or near-real-time and while the user is wearing the brace.

Embodiment 1—Fixed Tension

Hinge Assembly 1: In a first embodiment, the pivoting hinge assembly comprises two opposing, facing subunits, with a proximal (top) and distal (bottom) short end, and an anterior (front) and posterior (rear) side. Each subunit houses one gear that intermeshes with an opposing gear during articulated joint movement, e.g. a proximal and distal gear; at least one tensioning element extending between the subunits on the anterior side of the gears and fixedly connected on the band's ends to the posterior side of the subunits; and a connector on the medial and lateral side pinning the subunits together while allowing the gears to rotate. Tension may vary in the hinge depending on the strength of the tensioning element provided in the hinge assembly; this may be decided at the time of fabrication of the brace. Alternatively, the hinge may freely pivot without teethed gears.

Hinge Assembly—Embodiment 2—Adjustable Tension—Via Handle and Slider

Hinge Assembly 2: Various embodiments of the present disclosure further comprise a second embodiment of a hinge assembly for use in a brace as disclosed herein, or other knee brace for treating a medical condition that requires unloading of a joint. The hinge assembly of embodiment 2 is similar to embodiment 1, but with the addition of a handle or knob attached to a mechanism that enables the user to adjust the tension on one end of the tensioning element(s) in real-time or near-real-time and in aspects while the user is wearing the brace by pulling the handle or knob one direction, thereby increasing tension, and then decreasing or releasing tension by moving in another direction.

In one embodiment, the tensioning element(s) proximal end is attached to a slide member that moves vertically (e.g., proximally-distally or distally-proximally) to, in aspects, pull the band taut to increase its tension. For example, when a user moves a handle or other mechanism that is located on the outside portion of the hinge, above the knee (or in aspects below or beside the knee), it moves backward-posteriorly. This handle movement forces a connecting slide member to move up-proximally, thus stretching the proximal end of the tensioning element(s). Thus, in an embodiment, the user can increase the stability and/or stiffness and/or tension of the brace/hinge/tensioning element by moving the hinge handle backwards, then moving it forward-anteriorly to release or decrease the tension and make the brace more flexible, which may comprise a fuller range of motion. In other aspects, the handle may slide front to back, back to front, or diagonally. In aspects, the user can increase stability and/or stiffness and/or tension of the brace/hinge/tensioning element by moving the hinge handle forwards, upwards, downwards, sideways, or diagonally, and then releasing or decreasing tension by moving the handle in an opposite or different direction.

Hinge Assembly—Embodiment 3—Adjustable Tension Via Ratchet-Pawl

Hinge Assembly 3: In another embodiment, each subunit houses one gear that intermeshes with an opposing gear during articulated joint movement, e.g. a proximal and distal gear; and at least one tensioning element extending between the subunits on a side of the gears (or over or under the gears) and fixedly connected on the tensioning element's ends to the posterior side of the subunits. In aspects, a core bracket member completely or partially covers the tensioning element between the subunits' open space to protect the element(s), and to pin the gears together while continuing to allow them to move relative to one another.

This embodiment may further comprise a rotatable or linear ratchet-pawl member on the upper and/or lower frame of the brace to vary tension in the band or bands. The user can rotate the knob or slide a lever to different positions to pull the tensioning element(s) tighter while reducing their effective length; this may be accomplished by winding a part of the tensioning element, for example a wire, around a coil as the member is rotated. For example, rotating the ratchet-pawl members clockwise increases the tension in the hinge assembly, making it less flexible, off-loading more of the user's weight from the knee joint, and providing more stability. The user can then release the ratchet-pawl members by pulling up or pushing down on a knob or a deactivation lever that is co-located with the member (or turning the knob in an opposite or different direction or rotation); and/or, in turn, the user would then be able to rotate the knob in a second, opposite direction to relieve tension in the tensioning element stretched between the gears.

Hinge Assembly—Embodiment 4—Adjustable Tension—Spooled Wire

Hinge Assembly 4: The various embodiments of the present disclosure may further comprise another embodiment of a hinge assembly for use in a knee brace as disclosed herein, or other brace for treating a medical condition that requires unloading of the joint. The embodiment comprises one or more strands of tensioning elements with the elements' respective ends fixed in the distal subunit. The element(s) endpoint on the proximal end is pulled on by a wire that encircles it.

In this embodiment, a rotatable knob is connected to a spool of wire, for example, that pulls on the proximal end of the tensioning element as the user rotates the knob (if the knob is on the proximal portion; if knob is on the distal portion, the distal end is pulled). In aspects, the knob is rotatable to fixed positions so that the user is able to adjust the tension in the tensioning element to a desired level, and release the tension by rotating the knob in a different or opposite direction. In aspects, more turns or longer turns on the knob will result in higher tension in the tensioning element, and more off-loading of forces on the user's knee joint.

Hinge Assembly—Embodiment 5—Wire-Linked Bands with Adjustable Tension

Hinge Assembly 5: The various embodiments of the present disclosure further comprise another embodiment of a hinge assembly for use in a knee brace as disclosed herein, or other brace for treating a medical condition that requires unloading of a joint. This embodiment comprises one or more tensioning elements housed completely or partially within the frame of the brace in both the proximal and distal frame portions. The one or more tensioning elements are further connected to each other by a wire that stretches over the gear assembly, and one or both bands are connected to an adjustable tensioning mechanisms using another wire(s).

In this embodiment, equal tension should be applied to the one or more bands in the hinge assembly, and tension is generated within the frame of the brace to generate resistance to flexion. The adjustable tension mechanisms of embodiments, 2, 3, and 4, for example, as explained supra, are connected to at least one of the bands either directly or indirectly.

Method of Use—Embodiments 1-5

In various embodiments of the present disclosure, the amount of weight unloading (or resistance or tension generated in the brace) can readily be tailored to a user based on their size, weight, injury, therapeutic needs, and/or desired athletic performance. Braces as described herein are capable of being lightweight, robust, of a narrow side profile, and well-fitting to users. Unlike braces in the prior art, those disclosed herein can be narrow and lightweight so as to be worn under clothing, which is usually not possible for athletic performance braces. For these reasons, the brace can be ideal for a range of injury types and severity, as well as a way to enhance athletic performance.

The various embodiments of the knee brace of the present disclosure can be used, by way of non-limiting examples: prophylactically to prevent injury; to reduce joint pain (e.g., during normal activities, physical exercise, or athletic competition); to rehabilitate existing injuries; post-operatively (high tension braces to immobilize the joint to a comfortable level); as extension assist devices for medical conditions such as osteoarthritis, with some stability support for proper knee alignment through the range of motion; to enhance athletic performance (e.g., by applying force as a knee joint extends to, for example, add explosiveness as an athlete jumps or starts running); and/or to prolong the life of a natural knee afflicted with osteoarthritis or other knee injury, or to prolong the life of a prosthetic joint, possibly in order to delay, prevent, or avoid knee surgery.

Likewise, the knee brace and/or hinge assemblies disclosed herein are able to: reduce the weight, forces, and/or pressure on a knee joint when a user is load bearing on their legs, such as standing. And/or, the knee brace and hinge assemblies are able to provide knee extension assistance when walking, bending, moving from sitting to standing, exercising, etc.; therefore, the user has to exert less physical effort to move their knee between flexion and extension.

In an embodiment, the method of use for reducing load bearing on the knee joint comprises the steps of: attaching a knee brace of, for example, one of the embodiments listed above to a user's knee, comprising laying the inside surface of the brace vertical support comprising the upper and lower portions against a user's leg; and closing the brace straps or other way of connecting the brace to the user, such as multiple straps around the user's femur and multiple straps around the user's tibia; and, load bearing on the user's knee joint, wherein the load and/or pressure on the knee joint is reduced to the extent that the user experiences a reduction in pain or an improvement in movement as compared to load bearing without the knee brace.

A method of use further or alternatively comprises extension assistance, comprising the steps of the following when the user flexes a knee joint: stretching and generating a counter or restoring force at the hinge tensioning element to propel the hinge back from a bent, flexed position to a straight, extended position; wherein the brace reduces the amount of force required to be exerted by the user's leg and knee and associated muscles to return the brace hinge (and knee joint) to an extended position from a bent position; and wherein the load and/or pressure on the user's knee joint is reduced to the extent that the user experiences a reduction in pain or improved movement as compared to flexing and extending the user's knee without a knee brace.

In yet another embodiment, a method of use comprises: having a user activate a hinge mechanism to pull one end (or both ends) of the tensioning element(s) more taut to increase tension and stability in the hinge assembly and knee brace, and then to deactivate the mechanism when it is no longer needed (or decrease tension). Various embodiments of the hinge mechanism comprise: a handle or engaging piece attached to a sliding lever, wherein moving the handle backwards (or forwards, upwards, downwards, or diagonally) causes the sliding lever to move in manner to pull one end (or both ends) of the tensioning element(s) taut (e.g., see second embodiment, supra); a rotatable or linear ratchet-pawl mechanism on one or both ends of the hinge (or above or below or beside the hinge) that a user can move clockwise or counterclockwise (or up or down) to impinge the tensioning element(s) and increase tension therein, then release (see, e.g., third embodiment); and a rotatable knob connected to an internally housed spool of, in aspects, rigid line or wire that is attached to a folded tensioning element, wherein turning the knob pulls on the tensioning element to increase the band's tension, and rotating the knob in the opposite direction releases or decreases the tension (see, e.g., fourth embodiment).

Methods of Generating Tension

Tension may be generated in a hinge by drawing a tensioning element, which may be an elastic, semi-rigid, or rigid component or components, across a hinge or lever arm that results in the elongation of the tensioning element. The tension generated as a function of degrees of flexion or per degree of flexion may vary throughout the range of flexion to generate different force profiles and resulting device performance. This may be achieved by variation in hinge geometry such as including a cam on the hinge or the pathway of the band or tensioning element, or gears of different radii. The geometries of cams or gears of variable radii may be tailored to achieve a desirable unloading profile depending on the user's needs. For example, a cam or gear may have an exaggerated bulge as opposed to a flat shape, which will generate an increasing amount of tension per degree of flexion as the user proceeds through a range of motion because the tensioning element or wire connected to the tensioning element will travel further over the cam. The force profile may be, by way of example only, linear, logarithmic, or exponential. Cams or gears of different geometries may be built into the brace or rapidly engaged, disengaged, or interchanged using levers or switches to achieve different force profiles and performance as needed.

Overall tension or the adjustment of the force unloaded per degree of flexion could be changed by limiting the movement of elastic material or anchoring at various fractions of the length, therefore limiting the region of elongation. The radius of the gear, thickness of the band, length of the band, multiple of bands, and other attributes of the brace can be adapted to the user's knees.

Bands or tensioning elements may comprise smaller individual bands or bundles that may be activated in parallel to achieve varying degrees of tension and unloading.

The activation of one or more tensioning elements may or may not be accomplished electronically via piezoelectric sensors or other electronic signals activated manually or automatically.

This system of generating tension can be applied to other joints of the body that may or may not include geared or ungeared hinges. For example, flexion and extension in the wrist may be assisted in a similar manner by connecting an upper and lower component above and below the wrist joint that are operatively connected using a tensioning element that may or may not be adjusted with a rotational dial such as a BOA or other mechanism.

Tension may be applied across various mechanical joints within the device, such as ball-and-socket, condyloid, gliding, and saddle joints. It may be applied in one or multiple axes, and can be engaged or disengaged as a whole, or in one axis depending on user need. The joints alone or in combination with the tensioning mechanism may limit or allow movement in one or multiple axes to reproduce, augment or limit the natural movement of the anatomical joint to which the device is applied.

Generating Tension Across a Single Upright Hinge

A single upright knee brace may include a tensioning system. A single upright knee brace may provide valgus or varus unloading support by utilizing material flexibility, rigidity, and strength characteristics to apply forces in the desired location(s). For example, a brace designed to treat varus to relieve medial compartment osteoarthritis may apply a lateral force in the center of the brace. The curvature of the frame away from the leg will apply a medial force above and below the user's knee, resulting in a corrective or distractive force that will reduce pressure in the medial compartment. Alternatively, a valgus brace may pull the joint laterally to unload the medial compartment while applying a lateral force above and below the joint. These forces may occur in conjunction with a force that pushes or pulls the joint apart, allowing for less contact pressure between joint components, such as the femur and tibia in the tibiofemoral joint.

The amount of force and support may be based on user inputs such as self-reported pain levels and measured or estimated inputs such as Q-angle and radiographic information.

In embodiments, the single upright brace frame is designed to translate force optimally without the bulk and weight of a double upright brace. For example, in aspects, the proximal and distal posterior support is required and an anterior support is required above and below the knee. In aspects, the brace can be worn on the medial or lateral side of the leg. In aspects, the brace can treat varus or valgus from either the inside or outside of the leg. For the unloading variant, the tensioning element may be drawn over the hinge and tensioned using one or more elastic bands and a tension-locking mechanism such as a BOA dial or other tension-adjusting mechanism that may be placed on the upper or lower portion of the frame. The brace may be contoured around the leg and patella to prevent or minimize rotation around the leg and migration down the leg. An alternative version of this brace has a fixed tensioning element. A strapping system may be incorporated into the brace frame that provides or supports the varus or valgus correction, prevents rotation around the leg, prevents migration down the leg, and eliminates undesired torques that the joint may be subjected to.

A variant of the knee brace may use the same brace and tensioning system to generate tension or resistance in the opposite direction, as in it resists extension. The device may be used to assist users by increasing range of motion.

Bolt Action or Lever Mechanism as an Adjustable Tensioning System

An alternative method of tensioning a band or multiple bands is with a system of one or more levers. A lever or levers may be pulled in one direction to increase tension and hooked onto a latch to maintain tension. The lever may be unlatched by pulling in one direction and moved by pulling in the other direction. The lever may be located on the upper or lower member of the knee brace and may be on one or both sides of the knee brace. The lever is operatively connected to the tensioning element. The lever may involve lace or wire to connect to one or more tensioning elements and one or more pulleys may be involved.

Cam Mechanism as an Adjustable Tensioning System

The tension in the brace may also be adapted to individual users by adding a cam-like feature wherein the tensioning element is drawn over a part causing the band or lace or wire to travel a greater distance as a result of the cam than without it. The result of the implementation of this mechanism may be an increased amount of tension per degree of flexion and may be tailored to individual users. The cam system may be adjusted on inputs from radiographic information and assessed need for correction and support. The cam modifications may be fully or partially automated and incorporated into the design process of the brace, or modified after the brace has been fabricated. The cams themselves may be adjustable and are interchangeable, in aspects.

Internalized Band as an Adjustable Tensioning System

An alternative system involves a mechanism where tensioning elements are integrated within the brace frame rather than drawn over the hinge. These bands may occur as one or more and may be found in either or both the upper and lower members. The brace frame may involve a tensioning system that controls the amount of torque around the hinge.

Method of Joint Distraction to Generate Space in Between the Joint

In a knee brace as described herein, distraction can be accomplished between the tibia and femur in a number of ways. In aspects, one way is in a geared or ungeared hinge, the radius of the gear can vary with degrees of flexion. One example is as the degree of flexion increases, the distance between joint centers may also increase, thereby providing a separation force across the joint. A user may be assessed to determine the optimal variation in the gear radii. In embodiments, for a double upright knee brace, the gear radius on one side of the brace can differ from the gear radius on the other side. This method of joint distraction is also applicable for a single upright knee brace. This mechanism may or may not include a slot design that allows for limited direction of travel based on gear radius. The slot controls the direction of the distraction. A center cap encases the hinge and contains slots to support the hinge mechanism. These slots can be oriented in an optimal manner for the user's needs and may be linear or curvilinear.

The distraction hinge may or may not be associated with a tensioning system. When the brace does not include a tensioning system, tension may be applied to the center pin through the hinge to maintain close gear contact. A mechanism of restricting motion of the center pin through the slot such as a leaf spring or a clip or clips may or may not be implemented.

The vertical member may be elongated to increase distraction. In embodiments, this can be accomplished in a number of ways such as providing a telescoping vertical member where the distal end of a member and the proximal end of a member are increased or decreased in distance based on the user's needs. Another method according to the present invention is the use of a spiral rotating knob that can push the distal and proximal members apart. The result is an increased distance between the connection points of the upper portion and lower portion of the knee brace to the user's leg. This can also be accomplished electronically by a motor tensioning the system. The telescoping mechanisms can be located on the upper or lower or both portions of the knee brace. The system may rely on one or more pulleys.

Pivoting External Loops as a Mechanism to Secure Straps or Semi-Rigid Supports A pivoting external loop or pivoting D-ring is included wherein the D-ring component includes a slot for passage or connection to a strap or support which may be comprised of Velcro or another material. The pivoting member involves a partially approximately round component that allows for the position of the strap relative to the frame to pivot. The pivoting member either straps into or is embodied within the brace frame. The component may or may not be 3D printed and may or may not be printed within the existing structure. Alternatively, the D-ring may be continuously adhered directly to the brace frame and may be cast, injection molded, or 3D printed. The range of motion or positioning of individual D-rings can be customized or altered based on the user's needs or the position on the brace frame.

Method of Detailed Characterization of Knee for Brace Design

A user's knees may be characterized by qualitative assessment through various activities such as squatting or knee extension. Input to the brace design may be extracted from radiographs, x-rays, MRIs, 3D scans, or data collected from sensors. Additional inputs may include patient-reported pain score, Q-angle, measurement of adipose tissue, and radiographic information. Radiographic information may or may not be used to estimate the firm and soft tissue in the user's knees. Aspects of this process may be automated.

The radius of the gear, thickness of the tensioning element(s), length of the tensioning element(s), multiple of tensioning element(s), number of tensioning element(s), and other attributes of the brace can be adapted to the user's knees. The process of assessing the patient as a method of creating inputs for the desired brace design can be partially or fully automated. For example, the Q angle may be estimated by a knee scan or x-ray, and a patient may report a certain level of pain in one compartment of the knee, such as the medial tibiofemoral compartment. The design of the brace may be automated to modify the amount of force applied to the opposing joint compartment (lateral) and other points on the leg to alleviate pressure in the injured joint compartment. The device may engage or disengage and alter tension in response to EMG or other biometric data related to the user's movement and support or limit movement in a desired manner.

From inputs such as biometric or radiographic data, the nature of the user's injury can be characterized and elements such as Q-angle correction, amount of unloading force based on degree of flexion, torque profile for medial and lateral sides, and tension levels for medial and lateral sides may be determined. The nature of the injury for the knee's envelope of motion may be understood. This may be modeled based on a scan based on the range of motion of the joint.

Adjusting Joint Geometry/Gait Via Tensioning

The user's injury will be analyzed with data including but not limited to MRI scans, x-rays, qualitative information such as self-reported pain and region of joint, and biometric data such as BMI and Q-angle. The patient may be recorded and gait modeled as well. This information can be used through manual or automated processes to restore and improve joint geometry to reduce pain or enhance performance. The brace may automatically or partially automatically adjust to the user's needs.

Joint rotation and/or joint alignment may be influenced by varying tension across the hinge. Tension may be applied to one or both sides of the brace. If tension is applied on both sides of the brace, the tension may be equal or dissimilar to generate the desired torque profile for each side. The torque profile is designed based on the needs of the user's joint to restore or improve joint alignment and function. The size and geometry of the brace frame may be modified to flex the appropriate amount. Material choice such as plastic, metal, carbon fiber, or a combination thereof may be used to achieve the desired flexibility to support the goal of improving joint function. The amount of flexibility of the brace frame will be tailored to the needs of the user for fit and to assist with generating an unloading force. For example, a brace with a bowed frame with the center of the bow placed at the center of the side of the knee condyle will generate an unloading force in the compartment opposite of the side where the bow is contacting the knee joint.

The user's gait may be influenced to a healthier gait by generating an appropriate amount of tension. The information described in the previous section and sections herein can improve gait, alter walking pattern to reduce pain, increase stability, and reduce long-term wear on the joint.

Method of Securing Wire or Lace to Tensioning Element

The tensioning element within a brace may be either 3D printed based on an elastic polymer or elastic material such as rubber, or may be cast or injection molded from a similar material. The wire or lace or cable may be secured to the tensioning element by looping through a series of holes and knotting or tying off the lace or wire. Alternatively, the lace or wire may be knotted or placed within a hardened material such as an epoxy that is then integrated or bonded or attached to the elastic material. The region where the wire or lace attaches to the tensioning element may use a metal component that may be crimped or compressed to secure the wire or lace within the tensioning element or elements. A part to increase surface area may be tethered or attached to the wire or lace and inserted within the tensioning element to prevent the band or wire or lace from detaching. The system may be secured further by coating with a glue or hardening compound such as an epoxy to minimize the risk of detachment. The opposite end of the tensioning element may be anchored in position due to a change in geometry that would prevent the tensioning element from moving or dislocating. Alternatively, this part may be pinned, glued, pinched, or screwed in place to prevent dislocation.

Method of Securing Knee Orthosis to Ankle Orthosis

The braces described herein may involve connection to an ankle foot orthosis wherein the tensioning system for the knee brace may additionally be connected to the ankle orthosis. Alternatively, the position support or tension in the ankle orthosis may be controlled by a separate tensioning system on the knee portion of the orthosis or ankle portion of the orthosis. The knee orthosis may be operatively connected to the ankle orthosis by a plastic, metal, carbon fiber, or other structural material. The geometry of the orthosis may be based on a 3D scan from the patient's leg and/or foot. Corrections to the gait and points of support and pressure may also be based on information from the 3D scan. In aspects, for unloading Knee Ankle Foot Orthoses (KAFOs), the amount of loading assistance will be pre-set in the brace according to the size and strength of the tensioning elements based on the user's needs. When tensioning elements and a tension locking mechanism are used, the tensioning elements may be drawn over the hinge or hinges, or attached to a wire or wires that are drawn over or through the hinge. The devices may interface mechanically or structurally to generate dynamic and synergistic forces throughout the lower limb through a range of motion or gait. For example, the tensioning elements of the knee brace and ankle orthosis may be mechanically integrated so that as the knee reaches about 60° of extension, the ankle orthosis support provides dorsiflexion support. Additionally, the tensioning elements may communicate remotely via Bluetooth, WiFi, or other signaling means to work synergistically to support or direct gait.

Method of Making

The various embodiments of the present disclosure may use traditional manufacturing processes for knee braces, and/or 3D printing to produce prototypes or final versions of the components (such as the gears and/or subunits of the hinge assembly) to then be injection molded, extruded, pultruded, or may be entirely 3D modeled and/or printed, from parts to the entire brace. In an embodiment, the brace is sized to fit the user and can be form fitted to the user. Unique fabrication methods and materials make this form fitting brace possible. For example, two-dimensional or three-dimensional pictures, videos, or scans can be used to generate a model or a final product (or parts) that contours or fits the user's leg or other joint, and the properties of the material, in aspects, will have an amount of flexibility in the lateral direction, for example, and less flexibility in the direction of extension or extension depending on the purpose of the brace.

The fabrication technique of the braces herein allows the braces to include unexpected advantages not included in the prior art, including manufacturing and performance advantages. Therefore, an improved fitting brace that is higher functioning, safer, more effective, and more comfortable is possible by the invention taught herein. The fabrication methods and materials can also assist in keeping production costs lower than the prior art.

In addition to injection molding and 3D printing the frame of the brace, the brace may also be constructed entirely of a material that allows for it to be thermal molded around a specific patient's leg post-fabrication, or similarly, sections of the brace may be made of a material that can be thermal molded to produce a specific force on a patient's leg at a given location, for example providing varus/valgus support. Additionally, it may be desirable for the padding on the brace, whether it is 3D printed as an extension of the frame of the brace or separately adhered using another method, to be thermal moldable to a patient's leg. The benefit of this would be that the padding could possibly be switched out or modified (if it is not continuous with the brace) as the patient desires, without the need for refabrication of the brace. Pultrusion and extrusion techniques are also envisioned.

Unloading and Torque

The knee brace vertical support of the present disclosure differs from the prior art, including in that it unloads a significant amount of force that is normally applied within the knee. The basis for patellofemoral pain is that a large amount of force is distributed over a small area. Injuries to this surface can result in severe pain and defects/injuries, and the cartilage surface can degrade, thus exposing bone and nerves in an accelerated time frame. The tension-generating, unloading mechanisms in the present disclosure's knee brace address distributing forces experienced in the knee to other body parts and dampening the impact that would be painful to a joint afflicted with osteoarthritis. The effect of action of the brace is equivalent to a significant reduction of weight by the user; the most fundamental treatment for sufferers of osteoarthritis is weight loss.

The amount of force unloaded in a knee brace of the present disclosure is characterized by its relative torque measured about the hinge (e.g., in units of inch-pounds [in-lbs]), and the amount of weight unloaded or offset (in units of pounds [lbs]). For example, the general strength or tension of the knee brace of the present disclosure is generally broken down into three categories:

Low: below 3 lbs. unloaded
 Medium: range of 3-15 lbs. unloaded
 High: above 15 lbs. unloaded The reduced force in an OA afflicted knee joint via use of the present brace and/or hinge assemblies allows for deeper flexion of the user's knee that would normally be prohibited due to pain. This deeper flexion engages the user's quadriceps to an extent that would normally be avoided by the user due to debilitating pain, thus facilitating a user gaining strength through exercise. Additionally, the resistance generated by the brace can strengthen supporting soft tissue during exercise, for example the hamstring can be strengthened via a brace vertical support and/or hinge assembly as disclosed herein that resists tension on the quadriceps.

Use of Condyle Spacers

The knee brace described herein may include condyle pads that may or may not be increased or decreased in width depending on the severity of the varus or valgus alignment of the knee. Condyle spacers are used to shift the Q angle of the knee, or the angle of the femur relative to the tibia. A method of correlating the Q angle to the degree of varus and valgus has been developed, and this may automatically generate inputs into a digital model of the brace to be fabricated in order to sufficiently compensate for the medical condition.

In embodiments of the present invention, the condyle portions of the brace can be adjusted in a telescoping manner to increase or decrease pressure on one side of the joint. For example, a certified prosthetist orthotist may be required to evaluate the Q angle of a user's knee, and then assign a specific number of condyle spacers that should be inserted within the adjustable condyle hinge region of the brace. The condyle spacers may be inserted by removing the screws and caps of the condyle hinge and inserting the desired number of condyle spacers into the condyle region of the brace, and replacing the cap and screws after adjustment. This embodiment poses the advantage of being able to readjust or add to the width of the condyle region if a progressive treatment path is desired for a patient. Another variation involves sliding spacers of different sizes in a tongue-and-groove that may lock or snap into positon, and allow for rapid adjustment of the condyle spacing.

In additional embodiments of the present invention, a predetermined width of the condyle spacing region may be desired. In this embodiment, the width of the condyle region would not be expected to change throughout the course of treatment for the patient, and the width of the hinge would be determined during fabrication of the brace, such that the condyle hinge cap of the brace may have a thickness that is determined based on the desired correction of the Q angle of the knee.

Use of Sensors and Motors

The knee brace described herein may have sensors in place that measure and monitor the position of the brace relative to either or both the leg and another part of the brace. This position data can provide velocity and acceleration data that are used as inputs to a processor or monitoring system for the brace. Velocity and acceleration may be measured by positioning sensors or other sensors. This data may provide the basis for adjustment by a motor system to either assist or support a joint by increasing or decreasing tension.

Sensors may also be used to measure and monitor the amount of tension present in the brace or joint assistive device, and the amount of unloading force applied at the joint, including a variable amount that changes as the joint is extended or flexed. The analog value of the tension present at the joint may be converted to a digital signal in a variety of ways, such that the user of the brace has knowledge of how much tension is present in the brace at any given time, or as a change in tension is recognized by the sensor.

The sensor(s) may be fabricated on or within the brace. The sensor(s) may output a digital or electronic signal, and they may connect to one or more LED lights that may indicate the information about the brace such as the amount of force or tension in the brace at any given moment in time.

Additionally, the sensor(s) may be connected to one or more lights that light up different colors depending on the amount of force or tension in the brace; for example, the light may light up one color for maximum force and another color for a lighter amount of force.

The brace motor, sensor, and control processor system may also include a potentiometer, gear box of gearing system, and one or more servo arms or levers. The motor is operatively connected to the tensioning element through a system of gears or another method such as a screw, which can gather or release tension, based on inputs from sensors managed by a controller or processor.

The sensor(s) may also be connected to a screen on the brace that communicates information such as force generated within the brace, or weight unloaded by the brace, such as in a relevant unit value for the user. The sensor(s) may also be synced to an application on a smart device, such as a smartphone, tablet, or computer, that provides the user with feedback about the amount of force being applied by the brace, and/or the direction the joint is being overloaded in or the direction the joint is being flexed or extended. Data from these sensors may be logged and analyzed, used to identify patterns, and may be used as inputs to a controller that determines how motors should function in an assistive or supportive manner.

The sensors may also be connected to the tensioning mechanism; for example, using feedback from the sensors, the tensioning mechanism may loosen or tighten the tension in the tensioning elements based on the feedback it receives and a preset level of desired tension, as decided by the user. This would eliminate the need for the user to adjust the amount of tension present in the brace during use of the brace. In an embodiment, a user would set certain parameters and, based on feedback from the sensors as processed by a processor, the brace would be able to automatically adjust tension using motors, hydraulics, or microdrives, for example, or to alert the user to change resistance. In aspects, the sensors and related processor may be connected to a server or the internet, which may inform the processor of whether to adjust tension, or it may provide advice to the user about tension recommendations or other information related to treatment or use of the brace. Similarly, the sensors in adjunct with a processor may inform a doctor of the tension in the knee brace or other information from the brace and use of the brace so that a treating physician, for example, could diagnose the patient, monitor the patient, monitor the treatment, provide treatment options, warn the user of problems, adjust tension, determine when there is improper use of the brace, determine if an injury has occurred, monitor performance, etc. Thus, sensors used with a processor may be able to provide more automatic use and adjustment of the brace, including using software implemented predefined parameters to adjust tension or otherwise monitor and control use of the knee brace. The tension may also be adjusted electronically in the absence of sensors, where one button or input increases tension, and another button or input may decrease tension. This can be done with a toggle switch, rotatable knob, or touch button(s).

Electromyography (EMG) sensors may be used to activate a joint assistance mechanism to unload weight in the joint for which the device is applied. This may be done with or without other sensors and with or without motors. The degree of assistance may be modified and calibrated to the needs of the user.

BRIEF DESCRIPTION OF THE DRAWINGS

The above and other features, aspects, and advantages of the present invention will become better understood with regard to the following description, appended claims, and accompanying drawings where:

DETAILED DESCRIPTION OF EXEMPLARY EMBODIMENTS

As used herein, the term "proximal" is synonymous with top or upper, as in above the knee, or the side closest to the user's torso. Likewise, the term "distal" is synonymous with bottom or lower, as in below the knee, or the side furthest from the user's torso.

As used herein, the term "anterior" refers to the front of the knee and/or brace, and "posterior" the back. As seen in the figures when the hinge is oriented up-down, anterior is upward, and posterior is downward.

Throughout the following detailed description the same reference numbers refer to the same elements in all of the figures.

Knee Brace

Figure 1:
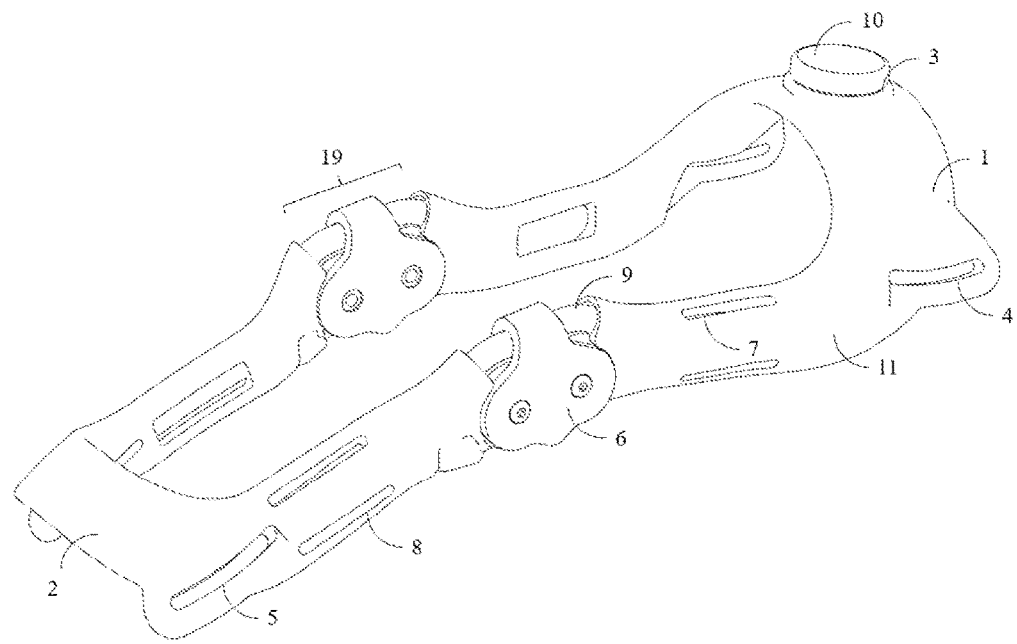
FIG. 1 is an illustration of the anterior left view of the knee brace frame in the extended position.

Table 1, infra, lists the components illustrated in FIG. 1 for the knee brace frame. The knee brace comprises a knee brace frame 11, or vertical support, a geared pivoting hinge assembly 19, and an adjustable tensioning mechanism 3. As illustrated in FIG. 1, the vertical support comprises: an upper (proximal) frame 1, and a lower frame 2. In this particular embodiment, both portions 1 and 2 fit to the front side, or anterior surface, of a user's leg just above and below their knee. In an embodiment, the knee brace frame 11 is sized small, medium, or large, depending upon the outer circumference of the user's thigh; or, the knee brace is custom designed and fabricated to fit a specific patient's knee, which can be performed by an electric digital scan. Normally, the diameter and circumference of the upper frame 1 is larger than that of the lower frame 2.

Straps: In aspects, the brace comprises straps. In this embodiment, the vertical support further comprises on the back, posterior side, of the knee brace 11, at least one horizontal strap above and below the knee to secure the brace to the user's leg. In one embodiment, two external loops exist on the posterior side of the upper frame and two external loops exist on the posterior side of the lower frame, wherein each frame has a loop on both the medial and lateral sides. At least one strap extends horizontally on the posterior side of the brace 11 between the brace upper portion 1's medial and lateral side and within the upper frame external loops 4, and at least one strap extends horizontally between the brace lower cuff 2's medial and lateral side and within the lower frame external loops 5.

TABLE 1

Knee Brace 11

| FIG. Item # | Component Name |
| --- | --- |
| 1 | Upper frame |
| 2 | Lower frame |
| 3 | Adjustable tensioning mechanism |
| 4 | Upper frame external posterior loops |
| 5 | Lower frame external posterior loops |
| 6 | Center cap |
| 7 | Upper frame internal strap loops |
| 8 | Lower frame internal strap loops |
| 9 | Tensioning element |
| 10 | Adjustable tensioning knob |
| 19 | Hinge assembly |

Hinge Assembly

Figure 2:
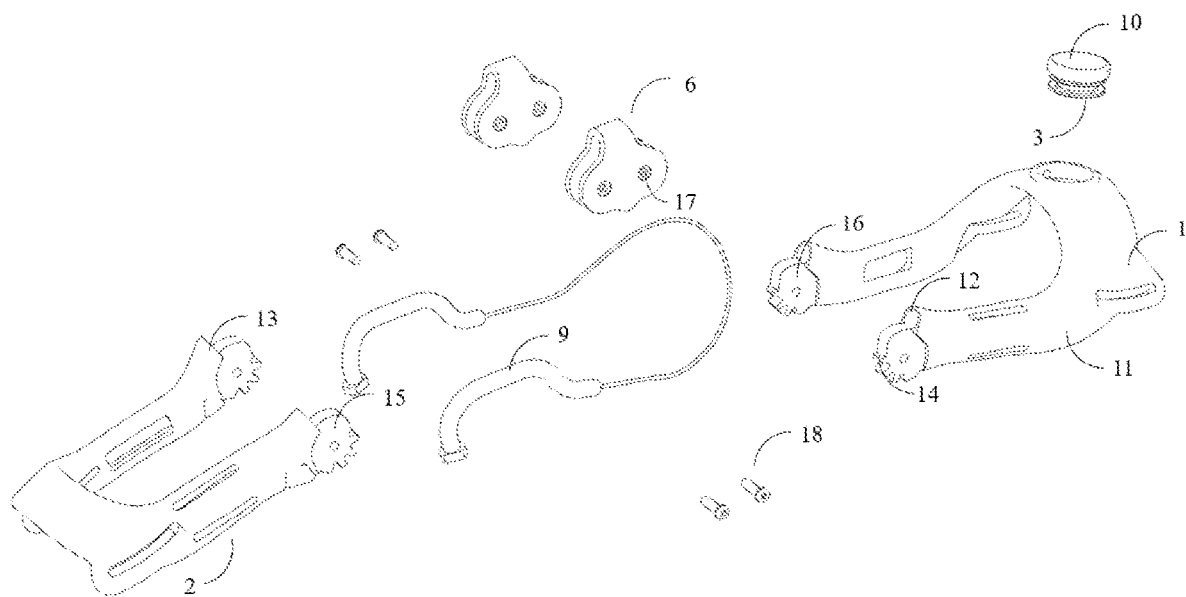
FIG. 2 is an illustration of an exploded view of the anterior left view of the knee brace frame in the extended position.

Table 2 lists the components illustrated in FIG. 2 for the hinge assembly. In aspects, the present disclosure comprises at least five different pivoting hinge assemblies, in aspects comprising at least one tensioning element 9, and two geared teeth, comprising a proximal gear 14 and a distal gear 15. Each type of hinge assembly can be used to generate tension in a one-sided brace (hinge medial or lateral side) or a full knee brace (hinge medial and lateral sides). In embodiments, the hinge assembly proximal end is connected to the brace upper frame 1, and the hinge assembly distal end to the lower portion 2, or in a similar manner to a variety of knee braces known in the prior art for unloading weight from the knee joint.

The two opposing gears (14, 15) of the hinge assembly 19, are connected via a center cap 6; the frame has a proximal opening 12 and a distal opening 13 that houses the tensioning element 9 and allows it to stretch across the intermeshing gears, resisting flexion. The teethed gears have a central hole 16, and the center caps have holes 17 in line with the gear central holes 16, which are functionally attached to a center core bracket 6 to allow for rotation around the gears while generating tension (or a breaking force, or a counter-restorative force), thus allowing the wearer of the brace to more easily flex and extend. The gears and the brackets may be functionally attached using screws, bolts, or another method known in the art 18. The center core brackets are positioned medial and lateral to the subunits, and are able to function to: pin the subunits together while enabling the gears to rotate in unison; protect the gears and tensioning element; and limit a maximum degree of flexion of the hinge assembly. In another embodiment, the element may be stretched under the gears, to assist with flexion; this may be used in a brace that is designed to help rehabilitate the knee after an injury.

The teethed gears further provide a mechanism to limit the maximum extension of the tensioning elements and hinge assembly to prevent hyperextension of the knee using extension and flexion stops and, in aspects, radially oriented slots. The slots allow for insertion of extension flexion stops, which are pre-made inserts that restrict the range of motion of the joint. The extension and flexion stops will not permit the gears or hinge to rotate further once contact is made with the stops. The allowable surface angle between the gears' point of contact is a design variable that can be modified to satisfy user requirements. Additionally, the extension and flexion stops may be designed in a way not present in the drawings; for example, the extension and flexion stops can be designed to fit between the gears on either the posterior or anterior side of the hinge assembly in order to limit the range of motion of the join.

TABLE 2

Hinge Assembly 19

| FIG. Item # | Component Name |
| --- | --- |
| 12 | Upper frame proximal thread hole |
| 13 | Lower frame distal thread hole |
| 14 | Proximal teethed gear |
| 15 | Distal teethed gear |
| 16 | Teethed gear central hole |
| 17 | Center cap hole |
| 18 | Fastener |

Figure 3:
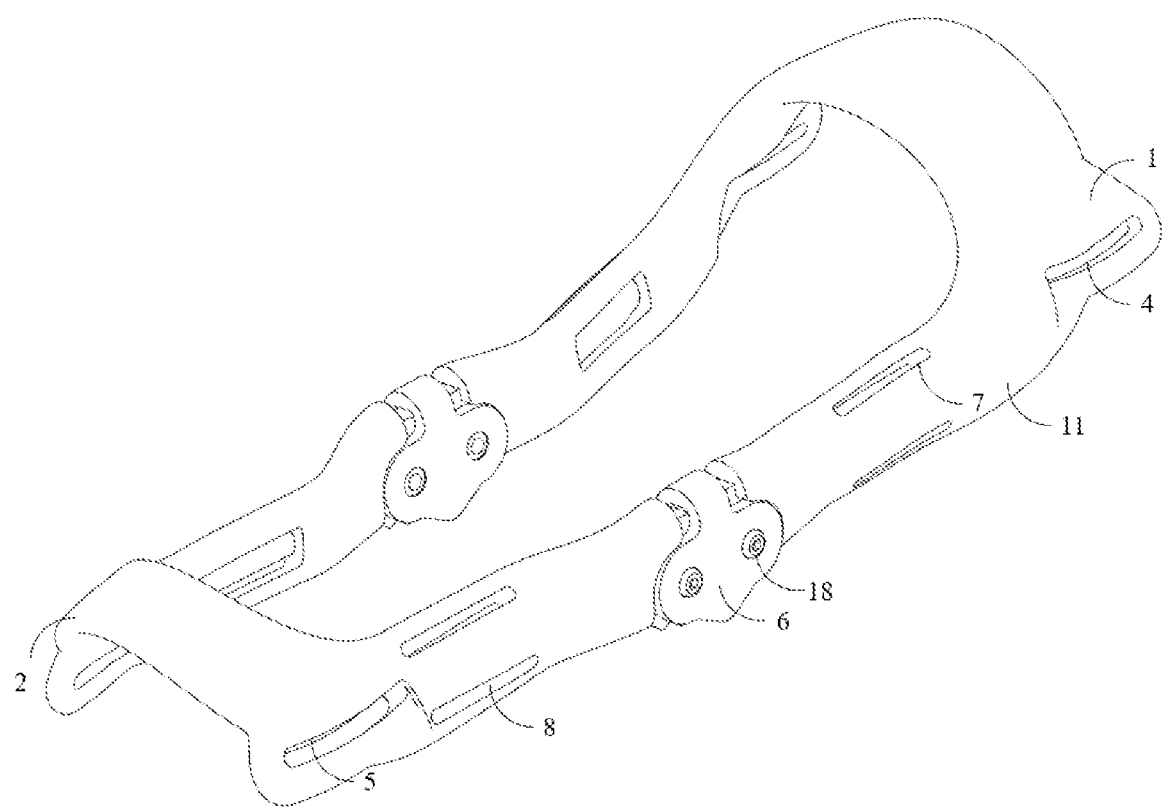
FIG. 3 is an illustration of an anterior left perspective view of the knee brace in the extended position with no adjustable tensioning mechanism.
Figure 4:
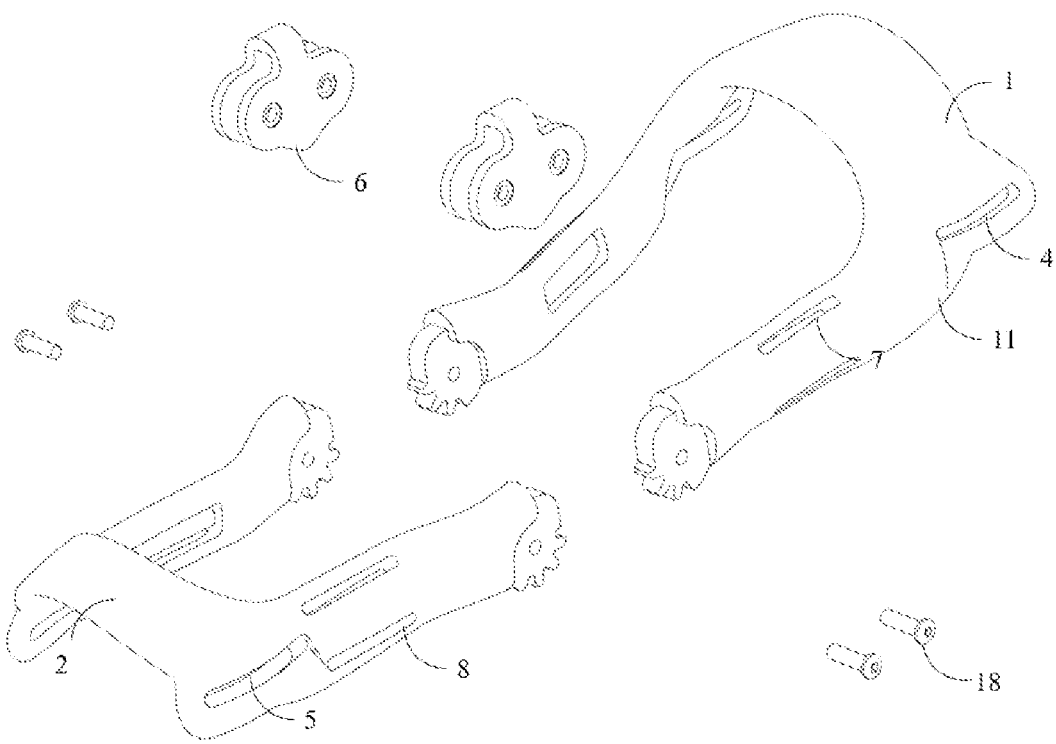
FIG. 4 is an illustration of an exploded view of the anterior left view of the knee brace with no adjustable tensioning mechanism.

The hinge assembly may incorporate at least one tensioning element 9 that is attached on each side of the upper and lower hinge assembly. The tensioning element stores energy when it is drawn across the hinge upon knee flexion by the wearer of the knee brace. The tensioning elements are ported through holes in the hinges (12, 13) or support members and are fixed in place in the brace on either the proximal or distal end, or both. Alternate designs are based on the needs of the user and include one or multiple tensioning elements within the hinge assembly on either or both the medial or lateral side of the knee brace, or above or below the hinge. These alternate designs also include bands of varying sizes that generate different amounts of resistance. Using more than one band can be tailored to engage and increase in tension as the degree of flexion is increased. An embodiment of the invention that does not include an adjustable tensioning system is illustrated in FIG. 3-4.

Figure 5:
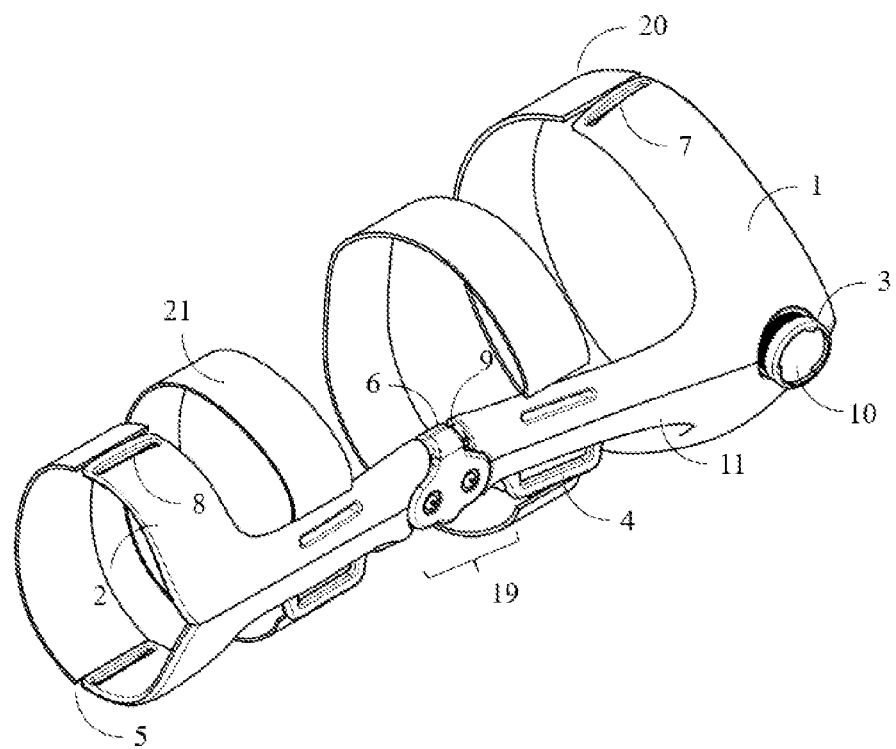
FIG. 5 is an illustration of a left side view of the single upright embodiment of the knee brace with a combination of rigid and semirigid supports.

As seen in FIG. 5, a single upright knee brace may include a tensioning system 3. A single upright knee brace may provide valgus or varus unloading support by utilizing material flexibility, rigidity, and strength characteristics to apply forces in the desired location(s). For example, a brace designed to treat varus to relieve medial compartment osteoarthritis may apply a lateral or medial force in the center of the brace at the hinge assembly 19. The curvature of the frames (1, 2) away from the leg will apply a medial or lateral force above and below the user's knee, resulting in a corrective or distractive force that will reduce pressure in the medial or lateral compartment.

The single upright brace frame is comprised of a proximal frame 1 and distal frame 2 connected with a center cap 6. In aspects, a combination of rigid or semi-rigid proximal and distal supports (20, 21) are required. In aspects, the brace can be worn on the medial or lateral side of the leg. In aspects, the brace can treat varus or valgus from either the inside or outside of the leg. For the unloading variant, the tensioning element 9 may be drawn over the hinge and tensioned using one or more elastic bands and a tension-locking mechanism 10 such as a BOA dial or other tension-adjusting mechanism that may be placed on the upper 1 or lower portion 2 of the frame. The brace may be contoured around the leg and patella to prevent or minimize rotation around the leg and migration down the leg with rigid or semirigid supports (20, 21). An alternative version of this brace has a fixed tensioning element. A strapping system may be incorporated into the brace frame (20, 21).

Figure 6:
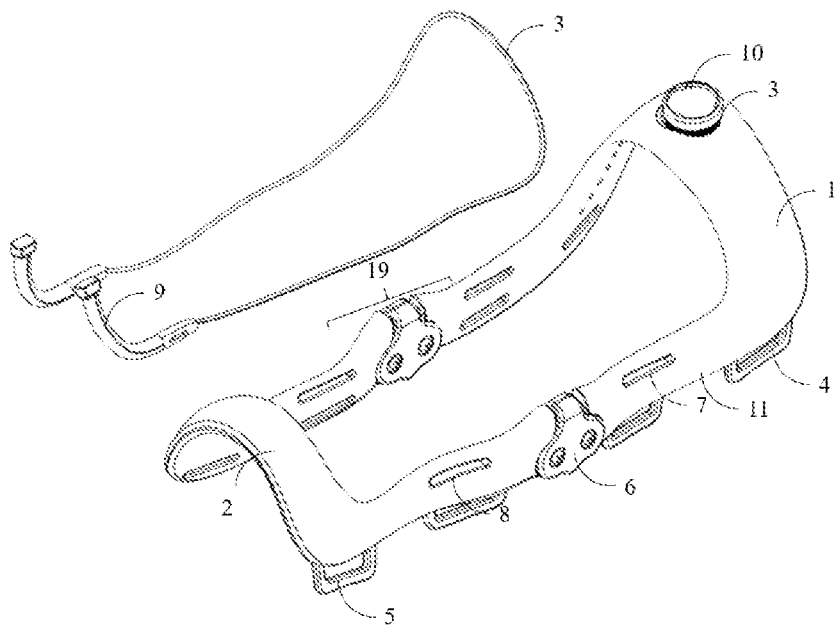
FIG. 6 is an illustration of an anterior left view of the knee brace embodiment with an internal adjustable tensioning mechanism.

As seen in FIG. 6, an alternative system involves a mechanism where one or more tensioning elements 9 are integrated within the upper portion 1 or lower portion 2 of the brace frame rather than drawn over the hinge. These bands may occur as one or more and may be found in either or both the upper and lower members. The brace frame may involve a tensioning system 3 that controls the amount of torque around the hinge 19.

Figure 7:
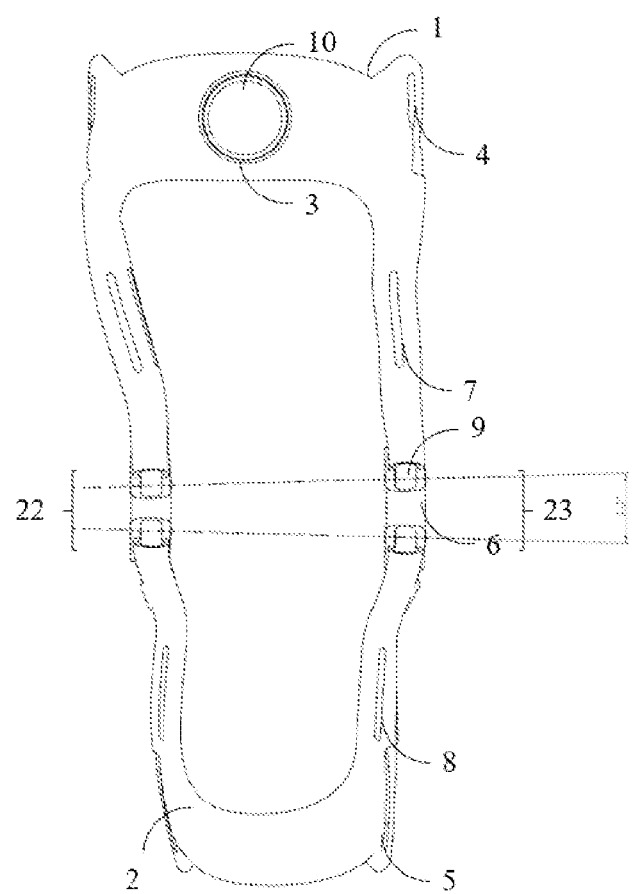
FIG. 7 is an illustration of the anterior view of a knee brace embodiment with teethed gears comprised of variable radii that provides joint distraction.
Figure 8:
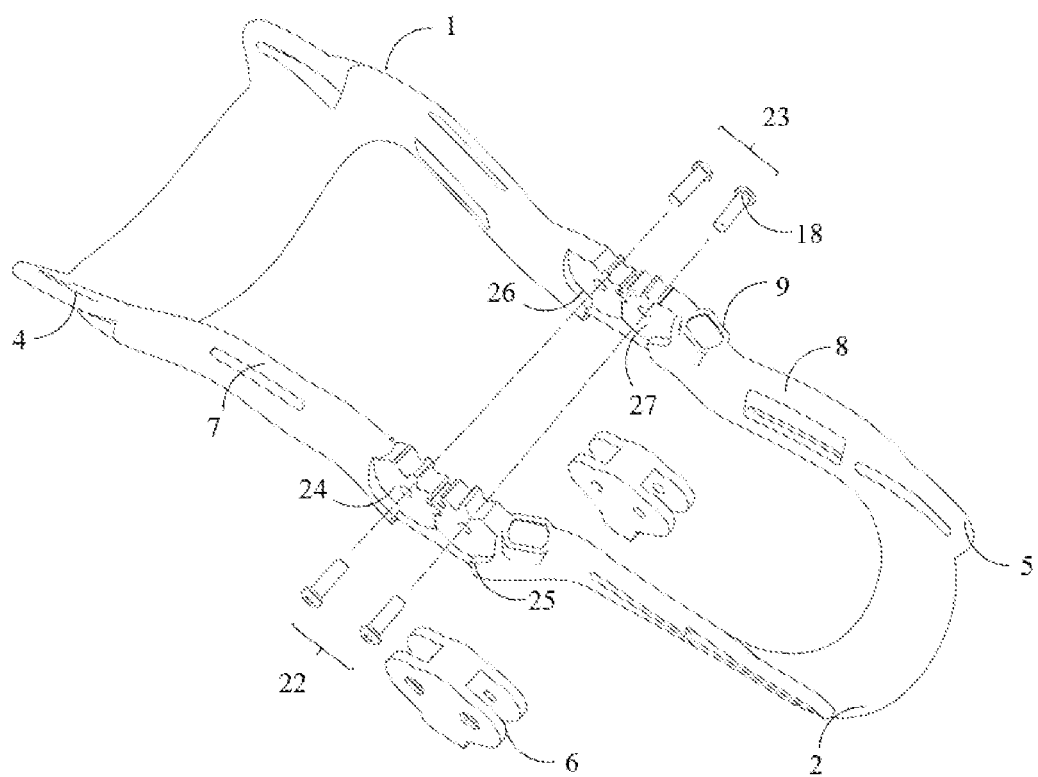
FIG. 8 is an illustration of the exploded, posterior right view of the knee brace embodiment with teethed gears comprised of variable radii.

An embodiment of the invention that includes hinge assemblies (22, 23) with gears of variable radii hinge as a means of distraction is seen in FIG. 7-8. The proximal and distal gear radii (24, 25) on one side of the brace and can differ from the gear radius on the other side (26, 27). This means of distraction is also applicable for a single upright knee brace.

Figure 9:
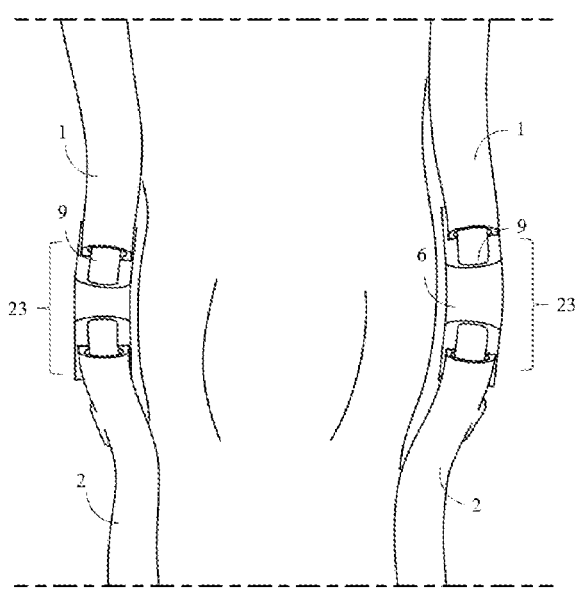
FIG. 9 is an illustration of the anterior view of a section of the knee brace embodiment with conforming gears and hinge caps and an adjustable tensioning mechanism.
Figure 10:
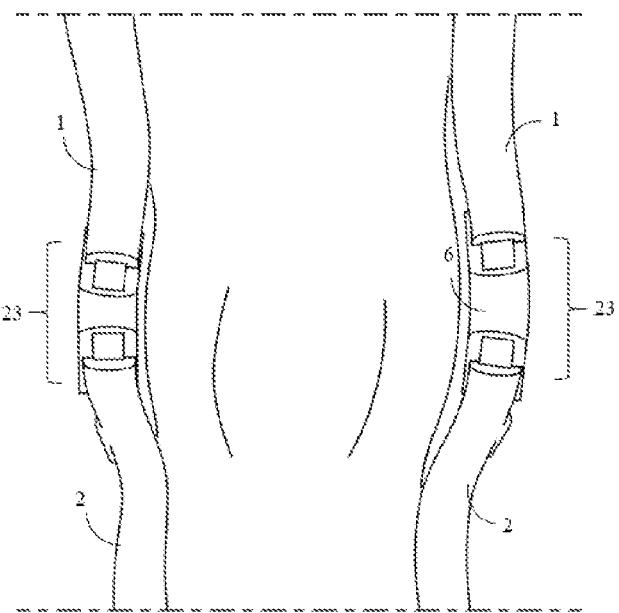
FIG. 10 is an illustration of the anterior view of a section of the knee brace embodiment with conforming gears and hinge caps without an adjustable tensioning mechanism or tensioning element over the hinge assembly.

As seen in FIG. 9, an embodiment of the invention includes a conforming hinge assembly 23 that may be tailored to achieve a desirable loading profile. The conforming hinge assembly may be comprised of proximal and distal gears, cam inserts, and hinge caps. The assembly may be curved to fully or partially conform to the user's joint or limb as opposed to a flat shape which will generate an increasing amount of tension per degree of flexion and the tensioning element 9 will travel further over the cam or gear mechanism. This embodiment may have an adjustable tensioning element as seen in FIG. 9 or no tensioning element as seen in FIG. 10.

Figure 11:
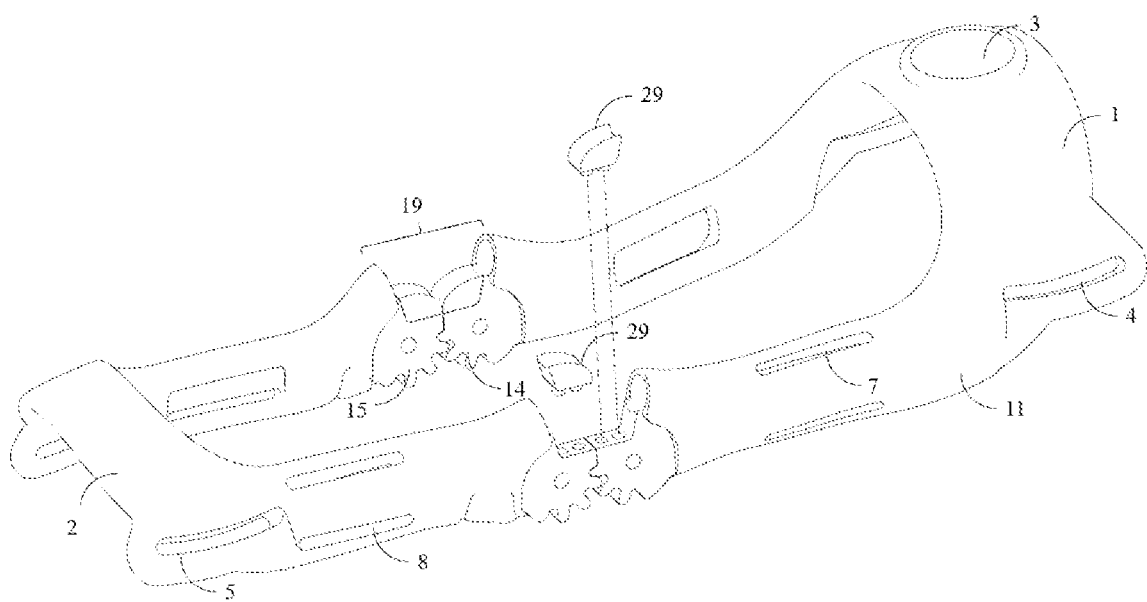
FIG. 11 is an illustration of the anterior left view of a knee brace frame as an embodiment with a cam mechanism as an adjustable tensioning system.
Figure 12:
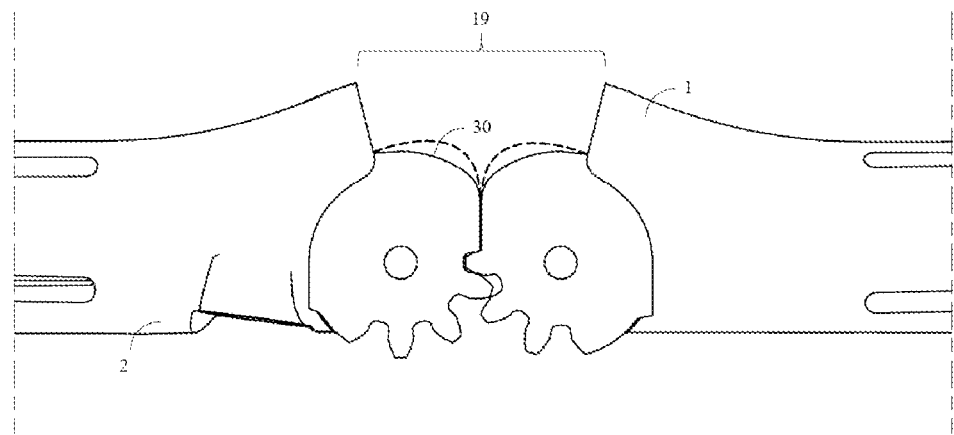
FIG. 12 is an illustration of a hinge section view of an embodiment of the knee brace frame with a cam mechanism as an adjustable tensioning system manufactured with 3D printing techniques.

As seen in FIG. 11, the subunits may further comprise cam units 29, e.g. located within the subunits as carved or molded into the internal housing of the subunits and residing slightly above-anteriorly to the gears so that the tensioning elements are drawn over the cams and the gears. The cam units increase the tension in the tensioning elements with increasing degrees of flexion of the user's knee. The cam geometry is variable and designed to generate a force that corresponds to unloading requirements. Alternatively, the cam profiles 30 may be manufactured and operatively embedded into the proximal and distal gears using 3D printing techniques as seen in FIG. 12.

Figure 13:
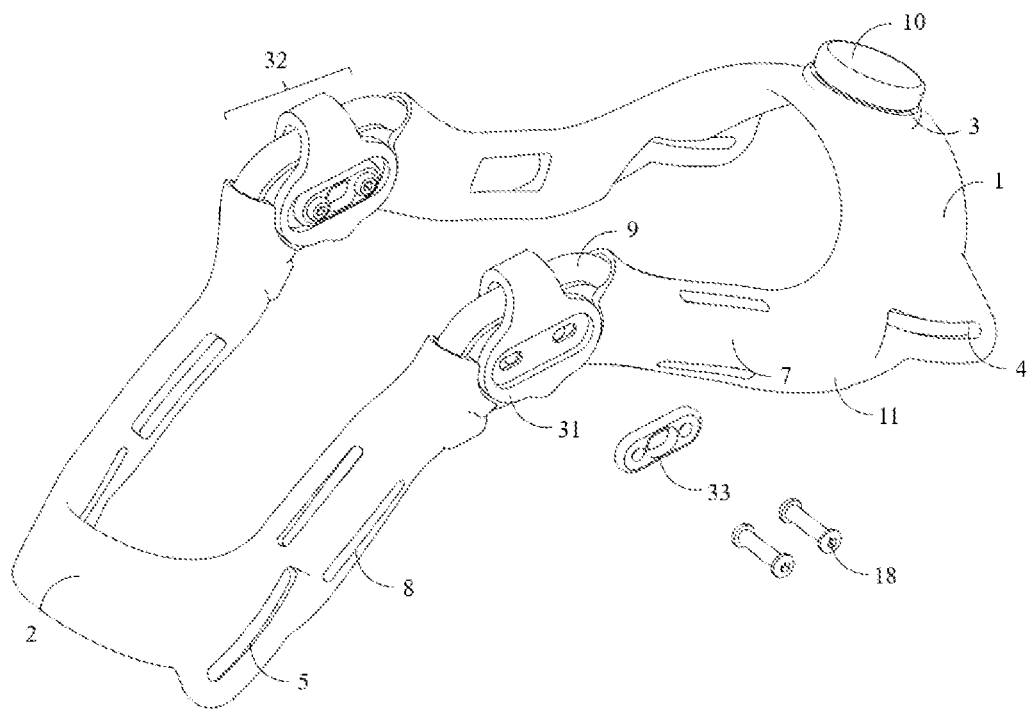
FIG. 13 is an illustration of an exploded anterior left view of the knee brace frame with a slot system as a means of distraction.
Figure 14:
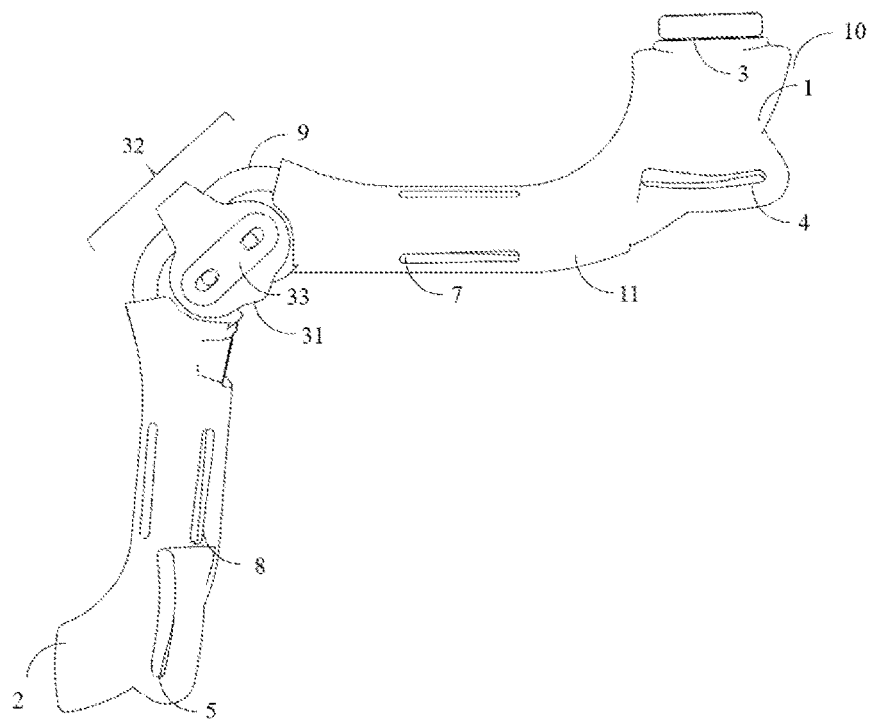
FIG. 14 is an illustration of a left view of an embodiment of a knee brace in flexion with a slot system as a means of distraction.
Figure 15:
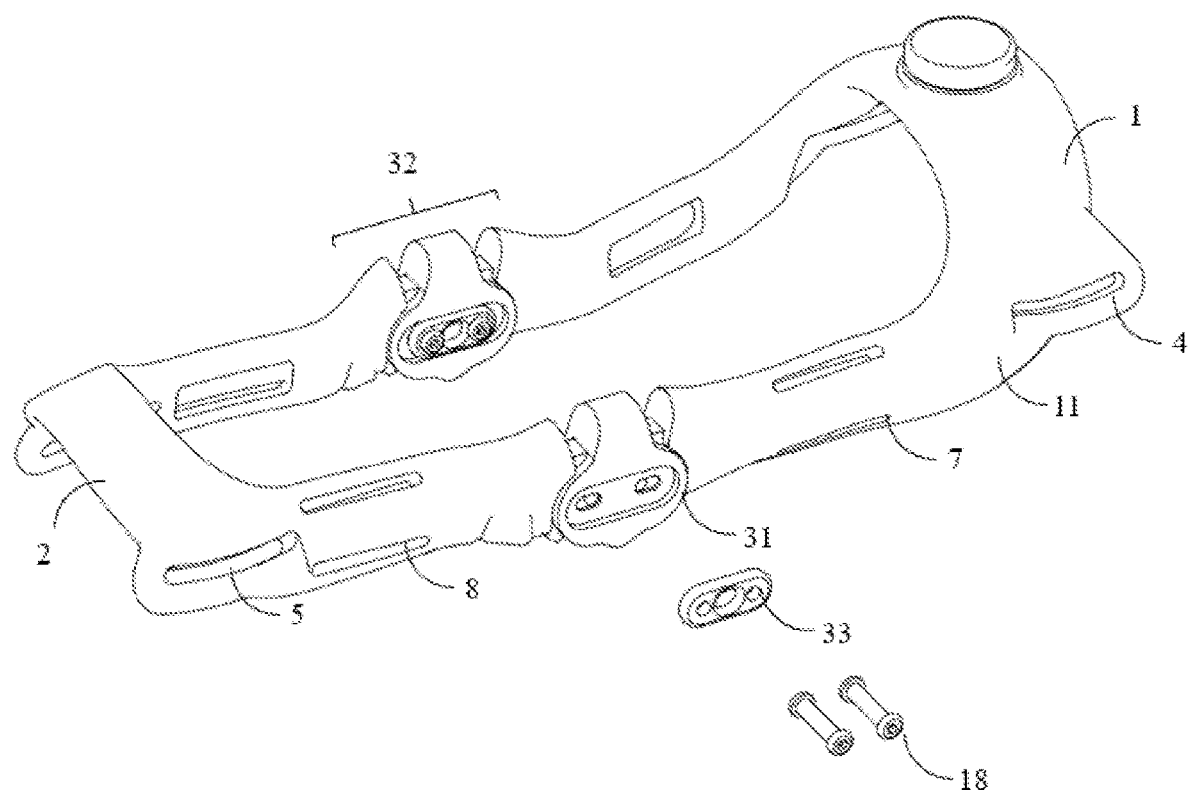
FIG. 15 is an illustration of an exploded anterior left view of the knee brace frame with a slot system as a means of distraction with no adjustable tensioning system.

An embodiment of this invention to create joint distraction involves a slot mechanism with a distraction hinge assembly 32 comprised of a distraction hinge cap 31 and distraction hinge center core bracket 33 as seen in FIG. 13 when the knee brace is in extension and FIG. 14 when the knee brace is in flexion. One or more slots in the center core bracket 33 circumscribe a pivot point of the hinge 32 which allows for limited direction of travel based on gear radius. The slots in the center core bracket 33 determine the direction of the distraction A center cap 31 encases the hinge and may contain slots to support the hinge mechanism. One or more fasteners 18 in the form of bolts, screws, or similar attachment mechanisms connects the center cap 31 to the upper 1 and lower portion 2 of the brace frame, and the center core bracket 33 or cap 31 comprises slots allowing the upper and lower portion to translate. This embodiment may or may not include an adjustable tensioning system. FIG. 15 illustrates one aspect of the distracting hinge mechanism with fixed tension.

Embodiments of the invention that include one or more sensors on the device, and in aspects a processor on or off the device, also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI), which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. Additionally, in aspects, the brace will allow the user to interact with it using other interfaces, such as, but not limited to, foot pedals, physical buttons, haptic feedback, or projected interface elements, and may include multiple interface options in combination with one another, to allow maximum flexibility in the ways the user can interact with the brace.

The invention described herein also includes, by way of example, the following Aspects:

Aspect 1: An unloading joint brace comprising the components of:
- a. a vertical support comprising an upper portion and a lower portion, wherein the upper portion comprises upper rigid, semi-rigid, or soft portions sized to fit a wearer's first body part adjacent to and above a wearer's joint; and wherein the lower portion comprises lower rigid, semi-rigid, or soft portions sized to fit a wearer's second body part adjacent to and below the wearer's joint;
- b. at least one pivoting hinge assembly, wherein a hinge assembly proximal end is connected to the upper portion and a hinge assembly distal end is connected to the lower portion;
- c. wherein the pivoting hinge assembly further comprises a proximal and a distal subunit with a posterior and anterior side, each subunit optionally housing a gear that intermeshes with an optional opposing gear during articulated joint movement;
- d. at least one tensioning element extended between the proximal and distal hinge subunits, wherein the at least one tensioning element is on or integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one tensioning element directly or indirectly attaches to the upper portion and where the at least one tensioning element directly or indirectly attaches to the lower portion, thereby reducing a load force or forces on a wearer's joint; and,
- e. wherein when the joint brace is a one-sided brace, then the hinge assembly is on one side of the wearer's joint; and, when the knee brace is a full brace, then the hinge assembly is on both sides of the wearer's joint.

Aspect 2: The unloading joint brace of Aspect 1, wherein the at least one tensioning element of the hinge assembly further comprises the at least one tensioning element extending between the subunits on an anterior side of the optionally housed gears, and wherein when there is more than one tensioning element, then the more than one tensioning elements are adjacent to one another and oriented in a longitudinal direction.

Aspect 3: The unloading joint brace of Aspect 1, wherein the unloading joint brace further comprises an unloading mechanism capable of enabling the wearer to engage and disengage, and/or increase and decrease the tension in, the at least one tensioning element.

Aspect 4: The unloading joint brace of Aspect 3, wherein the unloading mechanism comprises a slide member attached to the proximal end of the at least one tensioning element, and a knob or rotatable handle on an exterior surface of the hinge assembly, able to move the slide member and the at least one tensioning element proximal end upward upon a user rotating the knob or rotatable handle either clockwise or counter-clockwise, thereby increasing tension in the at least one tensioning element; and able to release the tension when the knob or rotatable handle is rotated in an opposite direction, wherein the knob or rotatable handle is able to be rotated to a plurality of positions that produce different levels of tension.

Aspect 5: The unloading joint brace of Aspect 3, wherein the unloading mechanism comprises,
- a rotatable ratchet-pawl system on a distal and/or a proximal end of the hinge assembly, able to anchor the at least one tensioning element to the rotating member, which upon rotation draws tension in the at least one tensioning element; and
- a disengagement member able to quickly release the ratchet-pawl system to reduce or release the tension.

Aspect 6: The unloading joint brace of Aspect 3, wherein the unloading mechanism comprises a knob or rotatable handle attached to the at least one tensioning element, wherein the knob or rotatable handle is moved a first direction that increases tension in the at least one tensioning element and can maintain tension by locking into one or more positions, and wherein tension can be reduced or released by moving the knob or rotatable handle into a second position.

Aspect 7: A joint brace with a pivoting hinge assembly, comprising,
   a. a proximal and a distal subunit, each subunit housing an optionally teethed gear;
   b. a distal and a proximal optionally teethed gear, wherein if gears are present they are able to intermesh during an articulated joint movement;
   c. at least one tensioning element with a proximal band end and a distal band end, wherein the at least one tensioning element extends between the subunits, with the distal band end affixed to the distal subunit and/or the proximal band end affixed to the proximal subunit; and,
   d. an adjustable unloading mechanism, wherein the hinge assembly is able to permanently and/or temporarily un-load a force or forces from a wearer's joint when the wearer moves back and forth between an extended and a flexed joint position, wherein the adjustable unloading mechanism is capable of allowing the wearer to increase and decrease the tension in the at least one tensioning element while the wearer is wearing the joint brace by shortening the at least one tensioning element, lengthening the at least one tensioning element, pulling on the at least one tensioning element, tightening the at least one tensioning element, releasing some or all tension on the at least one tensioning element, or combinations thereof.

Aspect 8: The joint brace with a pivoting hinge assembly of Aspect 7, wherein the unloading mechanism for extending the proximal end of the at least one tensioning element band comprises a slide member attached to the proximal end of the at least one tensioning element, and a rotatable handle on an exterior surface of the hinge assembly that is able to move the slide member and the at least one tensioning element proximal end upward upon a user rotating the rotatable handle, thereby increasing tension in the at least one tensioning element and able to release or decrease the tension when the rotatable handle is counter-rotated, wherein the rotatable handle is able to be rotated to a plurality of positions that produce different levels of tension.

Aspect 9: The joint brace with a pivoting hinge assembly of Aspect 7, wherein the unloading mechanism is attached to one or both ends of the at least one tensioning element, and the hinge assembly further comprises:
   a rotatable ratchet-pawl system on a distal and/or a proximal end of the hinge assembly, able to impinge the at least one tensioning element to prevent the band from stretching and to increase the tension in the at least one tensioning element; and
   a disengagement member able to release the ratchet-pawl system to reduce the tension.

Aspect 10: The joint brace with a pivoting hinge assembly of Aspect 7, wherein the subunits are spaced apart, and further comprising a center cap member or members residing between or housing the subunits and able to cover and protect the at least one tensioning element. A center cap can be comprised of one or more rigid or semi-rigid components such as a support or prong that may or may not encase a tensioning element. A center cap may be located on one or more sides of the hinge assembly.

Aspect 11: The joint brace with a pivoting hinge assembly of Aspect 7, wherein the adjustable unloading mechanism comprises a ratcheting-pawl member capable of allowing the wearer to position, set, or adjust the at least one tensioning element at or to a wearer selected tension.

Aspect 12: A method of unloading a force or forces from a joint by a wearer of a joint brace, the steps comprising:
   a. attaching the joint brace with a pivoting hinge assembly to a wearer's joint, wherein the pivoting hinge assembly comprises:
      a proximal and a distal portion, each portion housing a gear;
      a distal and a proximal gear able to intermesh during an articulated joint movement; and
      at least one tensioning element with a proximal end and a distal end, wherein the at least one tensioning element extends between the proximal and distal portions on an anterior side of the gears, with the distal band end affixed to the distal portion or the proximal band end affixed to the proximal portion; and
      wherein the joint brace comprises an adjustable unloading mechanism capable of increasing the tension on the at least one tensioning element, and wherein tension on the at least one tensioning element is created by applying a substantially equal pulling force or forces where the at least one tensioning element directly or indirectly attaches to the proximal portion and where the at least one tensioning element directly or indirectly attaches to the distal portion;
   b. engaging the unloading mechanism when the wearer requires increased stability and/or tension in the joint brace; and,
   c. disengaging or adjusting the unloading mechanism when the wearer no longer requires the increased stability and/or tension, or when the wearer no longer requires the same amount of increased stability and/or tension.

Aspect 13: The method of unloading a force or forces from a joint by a wearer of a joint brace of Aspect 12, wherein the unloading mechanism further comprises a slide member attached to the proximal end of the at least one tensioning element, and a rotatable handle on an exterior surface of the hinge assembly that is able to move the slide member and the at least one tensioning element proximal end upward upon a wearer rotating the rotatable handle, thereby increasing tension in the at least one tensioning element, and wherein the unloading mechanism is able to release or lower the tension when the rotatable handle is counter-rotated, and wherein the rotatable handle is able to be rotated to a plurality of positions that produce different levels of tension.

Aspect 14: The method of unloading a force or forces from a joint by a wearer of a joint brace of Aspect 12, wherein the unloading mechanism further comprises a rotatable ratchet-pawl system on a distal and/or a proximal end of the hinge assembly able to impinge the at least one tensioning element to prevent the at least one tensioning element from stretching and to increase the tension in the at least one tensioning element, and comprising a disengagement member able to release the ratchet-pawl system to reduce the at least one tensioning element tension.

Aspect 15: The method of unloading a force or forces from a joint by a wearer of a joint brace of Aspect 12, wherein the joint brace further comprises:
a. a vertical support comprising an upper portion and a lower portion with a medial and a lateral side, wherein the upper portion comprises,
   an upper unit sized to fit a wearer's body part adjacent to and above a user's joint;
   at least one strap capable of attaching the upper unit to the wearer's body part;
   wherein the lower portion comprises,
   a lower unit sized to fit a wearer's body part adjacent to and below the wearer's joint;
   at least one strap capable of attaching the lower unit to the wearer's body part;
b. wherein when the joint brace is a one-sided brace, then the hinge assembly is on the lateral or the medial side of the joint; and, wherein when the joint brace is a full brace, then the hinge assembly in on either or both the lateral or the medial side of the joint.

Aspect 16: The unloading joint brace of Aspect 1, wherein one or more of the components are three dimensionally printed, and/or the joint brace is custom sized using digital imaging of the wearer's joint or adjacent body part or parts.

Aspect 17: An unloading knee brace comprising the components of:
a. a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;
b. at least one pivoting hinge assembly, wherein a hinge assembly proximal end is connected to the upper portion and a hinge assembly distal end is connected to the lower portion;
c. wherein the pivoting hinge assembly further comprises a proximal and a distal subunit with a posterior and anterior side, each subunit optionally housing a gear that intermeshes with an optional opposing gear during articulated joint movement;
d. at least one tensioning element integrated within and extending between the proximal and distal hinge subunits, wherein the at least one tensioning element is capable of increasing a tension force within the at least one tensioning element when the hinge assembly is moved to a flexed position, thereby reducing a load force or forces on a user's knee;
e. wherein when the knee brace is a one-sided brace, then the hinge assembly is on the lateral or the medial side of the knee; and, when the knee brace is a full brace, then the hinge assembly is on the lateral side of the user's knee, the medial side of the user's knee, or both the lateral side and the medial side of the user's knee; and
f. wherein the hinge assembly further comprises:
   a cam unit co-located with the optionally housed gear within the subunit, and upon which the at least one tensioning element is drawn over the cam unit and the optionally housed gear to increase tension during knee flexion; and
   wherein the hinge assembly is prevented from hyperextending anteriorly by the proximal and distal subunit connecting on the subunits' anterior side.

Aspect 18: An unloading knee brace comprising the components of:
a. a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;
b. at least one pivoting hinge assembly, wherein a hinge assembly proximal end is connected to the upper portion and a hinge assembly distal end is connected to the lower portion;
c. wherein the pivoting hinge assembly further comprises a proximal and a distal subunit with a posterior and anterior side, each subunit optionally housing a gear that intermeshes with an optional opposing gear during articulated joint movement;
d. at least one tensioning element extended between the proximal and distal hinge subunits, wherein the at least one tensioning element is integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one tensioning element directly or indirectly attaches to the upper portion and where the at least one tensioning element directly or indirectly attaches to the lower portion, thereby reducing a load force or forces on a user's knee;
e. wherein when the knee brace is a one-sided brace, then the hinge assembly is on the lateral or the medial side of the knee; and, when the knee brace is a full brace, then the hinge assembly is on the lateral side of the user's knee, the medial side of the user's knee, or both the lateral side and the medial side of the user's knee; and
f. wherein the hinge assembly further comprises at least one connector positioned medial and lateral to the subunits, wherein the connector is capable of connecting the subunits together while enabling the optionally housed gears to rotate, and wherein if the subunits house an optional gear, the connector protects the optionally housed gears and the at least one tensioning element.

Aspect 19: An unloading knee brace comprising the components of:
a. a vertical support comprising an upper portion and a lower portion, wherein the upper portion comprises an upper rigid or semi-rigid curved unit sized to fit a user's femur adjacent to and above a user's knee joint; and wherein the lower portion comprises a lower rigid or semi-rigid curved unit sized to fit a user's tibia adjacent to and below the user's knee joint;
b. at least one pivoting hinge assembly, wherein a hinge assembly proximal end is connected to the upper portion and a hinge assembly distal end is connected to the lower portion;
c. wherein the pivoting hinge assembly further comprises a proximal and a distal subunit with a posterior and anterior side, each subunit optionally housing a gear that intermeshes with an optional opposing gear during articulated joint movement;
d. at least one tensioning element extended between the proximal and distal hinge subunits, wherein the at least one tensioning element is integrated within the proximal and distal hinge subunits and partially, mostly, or completely covered by the proximal and/or distal hinge subunits, wherein a first end of the at least one tensioning element is directly or indirectly attached to the upper portion and a second end of the at least one tensioning element is directly or indirectly attached to the lower portion, and wherein the at least one tensioning element is capable of increasing a tension force within the at least one tensioning element when the hinge assembly is moved to a flexed position by applying a substantially equal pulling force or forces where the at least one tensioning element directly or indirectly attaches to the upper portion and where the at least one tensioning element directly or indirectly attaches to the lower portion, thereby reducing a load force or forces on a user's knee;
e. wherein when the knee brace is a one-sided brace, then the hinge assembly is on the lateral or the medial side of the knee; and, when the knee brace is a full brace, then the hinge assembly is on the lateral side of the user's knee, the medial side of the user's knee, or both the lateral side and the medial side of the user's knee;
f. wherein the unloading knee brace further comprises an unloading mechanism capable of enabling the user to engage and disengage, and/or increase and decrease the tension in, the at least one tensioning element; and
g. wherein the at least one tensioning element is connected on one end to the distal or proximal subunit, and the unloading mechanism comprises:
a substantially inelastic line or wire attached to the at least one tensioning element on a first end, and to a spool on a second end; and
a spool operatively connected to an external rotatable knob;
wherein the user is able to increase the tension in the at least one tensioning element by rotating the knob in a first direction, and wherein the substantially inelastic line or wire is connected to the spool; and,
wherein the user is able to decrease the tension by rotating the knob in an opposite or second direction, or by releasing a ratchet pawl system mechanism or a locking flange washer system operatively connected to the knob.

Aspect 20: A knee brace or an elbow brace with a pivoting hinge assembly, comprising,
a. a proximal and a distal subunit, each subunit housing a teethed gear;
b. a distal and a proximal teethed gear, wherein the gears are able to intermesh during an articulated joint movement;
c. at least one tensioning element with a proximal band end and a distal band end, wherein the at least one tensioning element extends between the subunits with the distal band end affixed to the distal subunit and/or the proximal band end affixed to the proximal subunit; and,
d. an adjustable unloading mechanism, wherein the hinge assembly is able to permanently and/or temporarily un-load a force or forces from the user's knee or elbow when the user moves back and forth between an extended and a flexed knee or elbow position, wherein the adjustable unloading mechanism enables the user to increase and decrease the tension in the at least one tensioning element;
e. wherein the adjustable unloading mechanism comprises the ability to increase the tension by:
pulling on the at least one tensioning element;
adding more tensioning elements of a same or of a different level of tension and/or diameter as the at least one tensioning element, wherein when there is more than one tensioning element, then the tensioning elements are adjacent to one another in a longitudinal orientation;
substituting the at least one tensioning element with one or more stiffer tensioning element(s);
folding the at least one tensioning element and extending an tensioning element center point until the at least one tensioning element is taut or more taut; and/or
using multiple tensioning elements set to engage at different degrees of flexion.

Aspect 21: A knee brace or an elbow brace with a pivoting hinge assembly, comprising,
a. a proximal and a distal subunit, each subunit housing a teethed gear;
b. a distal and a proximal teethed gear, wherein the gears are able to intermesh during an articulated joint movement;
c. at least one tensioning element with a proximal band end and a distal band end, wherein the at least one tensioning element extends between the subunits, with the distal band end affixed to the distal subunit and/or the proximal band end affixed to the proximal subunit; and,
d. an adjustable unloading mechanism, wherein the hinge assembly is able to permanently and/or temporarily un-load a force or forces from the user's knee or elbow when the user moves back and forth between an extended and a flexed knee or elbow position, wherein the adjustable unloading mechanism enables the user to increase and decrease the tension in the at least one tensioning element;
e. wherein the unloading mechanism comprises,
the at least one tensioning element attached on either end of the one or more tensioning element to either the proximal subunit, the distal subunit, or both;
a wire anchored to the at least one tensioning element connected to a spool;
wherein the spool is connected to an external rotatable knob;
wherein the user is able to increase the tension in the at least one tensioning element by rotating the knob in one direction, wherein the wire and the at least one tensioning element are pulled taut or more taut; and,
wherein the user is able to decrease the tension by rotating the knob in a second direction, or by releasing a ratchet pawl mechanism or a locking flange washer system.

Aspect 22: A method of unloading a force or forces from a knee by a user of a knee brace, the steps comprising:
a. attaching a knee brace with a pivoting hinge assembly to a user's knee, wherein the pivoting hinge assembly comprises:
a proximal and a distal portion, each portion housing a gear;
a distal and a proximal gear able to intermesh during an articulated joint movement; and at least one tensioning element with a proximal band end and a distal band end, wherein the at least one tensioning element extends between the proximal and distal portions on an anterior side of the gears, with the distal band end affixed to the distal portion or the proximal band end affixed to the proximal portion; and wherein the knee brace comprises an adjustable unloading mechanism capable of increasing the tension on the at least one tensioning element, and wherein tension on the at least one tensioning element is created by applying a substantially equal pulling force or forces where the at least one tensioning element directly or indirectly attaches to the proximal portion and where the at least one tensioning element directly or indirectly attaches to the distal portion;

b. engaging the unloading mechanism when the user requires increased stability and/or tension in the knee brace; and, c. disengaging or adjusting the unloading mechanism when the user no longer requires the increased stability and/or tension, or when the user no longer requires the same amount of increased stability and/or tension;

d. wherein the unloading mechanism comprises,
the at least one tensioning element on a first end to the proximal portion or the at least one tensioning element attached on a first end to the distal portion;
a wire attached on a second end of the at least one tensioning element, wherein the wire is attached to a spool;
wherein the spool is connected to an external knob;
wherein the user is able to increase the tension in the at least one tensioning element by rotating the knob in a first direction, wherein the wire and the at least one tensioning element are pulled taut or more taut; and,
wherein the user is able to decrease the tension in the at least one tensioning element by rotating the knob in a second direction and/or by releasing a ratchet-pawl mechanism or a locking flange washer system.

Aspect 23: An unloading joint brace comprising:

a. a proximal and a distal subunit, each subunit housing a pivot joint or teethed gear, wherein the gears are able to intermesh during an articulated joint movement;

b. at least one tensioning element with a proximal band end and a distal band end, wherein the at least one tensioning element extends between the subunits with the distal band end affixed to the distal subunit and/or the proximal band end affixed to the proximal subunit; and, c. an adjustable unloading mechanism, wherein the pivot point is able to permanently and/or temporarily un-load a force or forces from a wearer's joint when the wearer moves back and forth between an extended and a flexed joint position, wherein the adjustable unloading mechanism enables the wearer to increase and decrease the tension in the at least one tensioning element;

d. wherein the adjustable unloading mechanism comprises the ability to increase the tension by:
 i. pulling on the at least one tensioning element;
 ii. adding more tensioning elements of a same or of a different level of tension and/or diameter as the at least one tensioning element, wherein when there is more than one tensioning element, then the tensioning elements are adjacent to one another in a longitudinal orientation;
 iii. substituting the at least one tensioning element with one or more stiffer tensioning element(s);
 iv. folding the at least one tensioning element and extending a tensioning element center point until the at least one tensioning element is taut or more taut; and/or
 v. using multiple tensioning elements set to engage at different degrees of flexion.

Aspect 24: A joint brace, comprising:

a. An upper frame and lower frame, connected by at least one unicentric or bicentric hinge, comprising one or more tensioning elements capable of increasing torque in the hinge and generating a force that opposes flexion of the joint;

b. wherein the hinge may optionally comprise intermeshing gears that interact when a wearer flexes the joint, and wherein the hinge is optionally adjacent to one or more side plates, caps, or hinge capsules that house the optional gears;

c. wherein the one or more tensioning elements are in series or parallel, and wherein the one or more the tensioning elements are connected to an adjustable tensioning mechanism, anchored to a point on the brace, contained within one or more tubes in either or both the upper frame or the lower frame, weaved through holes in either or both the upper frame or the lower frame, connected to each other when there are multiple tensioning elements, and/or connected to one or more wires that extend over the hinge of the brace; and d. wherein the brace may optionally comprise at least one tensioning element stretching over the hinge, and wherein the at least one optional tensioning element is drawn with increasing degrees of flexion or extension so that it is capable of being connected to a tensioning mechanism.

Aspect 25: The unloading joint brace of claim 23 or 24, wherein the one or more tensioning elements comprise one or more elastic bands or one or more springs.

Aspect 26: A joint brace, comprising:

a. An upper frame and lower frame comprising one or more tensioning elements, connected by at least one unicentric or bicentric hinge, comprising one or more tubes or holes integrated partially or completely within or on the upper or lower frame, wherein the one or more tubes or holes is capable of containing the one or more tensioning elements;

b. Wherein the one or more tensioning elements are optionally secured or protected by the one or more tubes or holes;

c. Wherein the one or more tensioning elements are optionally inserted or weaved through the one or more holes to secure the one or more tensioning elements to the upper frame or lower frame or to keep the one or more tensioning elements in place on the upper frame or lower frame;

d. wherein the one or more tensioning elements are connected to each other or anchored to the joint brace, connected to a tensioning mechanism, or connected to one or more wires that are positioned across the hinge of the brace, and wherein the one or more tensioning elements are capable of increasing torque in the hinge and generating equal forces on both the upper and lower side of the hinge that oppose flexion of the joint;

e. wherein the hinge may optionally comprise intermeshing gears that interact when a wearer flexes the joint, and wherein the hinge is optionally adjacent to one or more side plates, caps, or hinge capsules that house the optional gears; and f. wherein the one or more tensioning elements are optionally anchored to fixed points in the upper frame or the lower frame, or to an adjustable tensioning mechanism.

Aspect 27: A knee or elbow brace frame capable of generating torque in a hinge, comprising:

a. An upper frame and lower frame, that may operatively connect at a joint via a variety of interlocking mechanisms, such as a tongue and groove mechanism or intermeshing gears, wherein the upper frame and lower frame can rotate relative to each other b. a system of various tensioning elements either partially or fully integrated within tubes in the frame or operatively connected to the frame of the brace that generate tension upon either flexion or extension depending on the tensioning element orientation, and may optionally be combined with an adjustable tensioning mechanism;

c. a network of rings and holes incorporated within the frame of the brace to allow for the attachment of straps to secure the brace to a user's limb, such as a buckle method, where the female end may be located incorporated in the frame of the brace.

Aspect 28: The unloading joint brace of Aspect 1, where the tensioning element extends across the hinge of the brace.

Aspect 29: A brace frame for a human joint comprising a hinge and an at least two frame components, wherein the hinge comprises one or more slots on the distal and proximal end of frame components allowing for a degree of flexion or extension in a range of up to −5 to up to 160 degrees, wherein the one or more slots are capable of being used to control the amount of extension and flexion of the hinge, wherein the one or more slots circumscribe a pivot point for the hinge, and wherein inserts can be inserted in the one or more slots to restrict the degree of flexion and/or extension of the human joint.

Aspect 30: The brace frame for a human joint of Aspect 29, wherein the inserts comprise different sizes and wherein the different sizes cause varying amounts of extension or flexion limits based on their size.

Aspect 31: The brace frame for a human joint of Aspect 29, wherein the one or more slots are capable of securing the inserts in the one or more slots despite articulated joint movement, and wherein the inserts are held in place by one or more side plates, caps, hinge capsules, or combinations thereof.

Aspect 32: The brace frame for a human joint of Aspect 29, wherein the inserts are inserted below the hinge, and wherein the inserts provide flexion or extension limitation.

Aspect 33: The brace frame for a human joint of Aspect 29, further comprising padding for the brace, wherein the padding may be three-dimensionally printed, and wherein a lattice of the padding is capable of being tailored to provide a desired amount of cushion for a given user or application.

Aspect 34: The brace frame for a human joint of Aspect 33, wherein the padding comprises a hook-and-loop or mushroom pattern, which may be printed directly on the brace frame.

Aspect 35: A method of making a brace for a human joint, comprising:

a. three-dimensionally scanning the human joint and providing a three-dimensional scan or image;

b. automatically determining from the three-dimensional scan or image the brace, upper frame, or lower frame design, size, weight, or shape;

c. scaling the design, size, weight, or shape of the brace, upper frame, or lower frame design to fit the human joint based on the three-dimensional scan or image.

Aspect 36: The method of making a brace for a human joint of Aspect 35, further comprising automatically generating the brace, upper frame, or lower frame and fitting the brace, upper frame, or lower frame to a user's joint, and designing the brace, upper frame, or lower frame to compensate for injuries to the leg based on the three-dimensional scan or image, including adding or decreasing pressure on one or more sides of the human joint.

Aspect 37: The method of making a brace for a human joint of Aspect 35, wherein the design, size, weight, or shape of the brace, upper frame, or lower frame is tailored or formed by computer-implemented software to account for and treat an injury, including depending on a severity of an injury, a type of injury, an injury treatment, and/or needs of a wearer.

Aspect 38: The unloading joint brace of Aspect 1, wherein the upper frame and/or lower frame is three-dimensionally printed, injection molded, pultruded, extruded, machined, or a combination thereof.

Aspect 39: The unloading joint brace of Aspect 1, wherein the upper frame and/or lower frame is thermal molded to adapt to a wearer's leg size or shape, or wherein the brace comprises components or sections comprising material(s) capable of being molded or sculpted using heat or light.

Aspect 40: The unloading joint brace of Aspect 1, further comprising padding, wherein all of or parts of a material used for the padding are capable of being thermal molded to fit a wearer's leg.

Aspect 41: The unloading joint brace of Aspect 1, wherein additional force is applied on an opposing side or on a side opposite of unicompartmental osteoarthritis in a wearer, and wherein a resting position of the brace applies a force to treat unicompartmental osteoarthritis, and wherein the force applied may be a result of modifications to brace frame geometry.

Aspect 42: The unloading joint brace of Aspect 1, further comprising one or more side plates, caps, or hinge capsules, wherein the one or more side plates, caps, or hinge capsules are used for increasing force on a condyle opposite to unicompartmental osteoarthritis in the wearer.

Aspect 43: The unloading joint brace of Aspect 1, further comprising hinge cap(s), wherein the hinge cap(s) comprise a removeable cap and screws allowing for a variable number of condyle spacing pads to be placed within the hinge cap(s) to act as a condyle shim.

Aspect 44: The unloading joint brace of Aspect 43, wherein the hinge cap(s) comprise an additive shim that attaches to the hinge cap(s) to increase condyle spacing to be placed within the hinge cap(s) to act as a condyle shim.

Aspect 45: A joint brace comprising one or more tensioning elements and an adjustable tensioning mechanism, wherein the adjustable tensioning mechanism is coupled to the one or more tensioning elements, wherein the adjustable tensioning mechanism comprises an interface between the adjustable tensioning mechanism and a wearer, and may include a knob, slide, button, tab, digital screen, processor, controller, motor, microdrive, switch, pulley, block and tackle system, or lever, that the wearer can use to adjust an amount of tension in the one or more tensioning elements; wherein adjusting the adjustable tensioning mechanism increases or decreases tension; and wherein the adjustable tensioning mechanism is held in a static position until a wearer changes tension.

Aspect 46: The joint brace of Aspect 45, further comprising one or more sensors that measure and monitor the position of the brace, wherein the one or more sensors are optionally capable of measuring and monitoring velocity or acceleration, wherein the position data, velocity data, or acceleration data, are used as input to a processor or monitoring system for the joint brace, and wherein the position data, velocity data, or acceleration data is used to instruct a motor or other tensioning system on the joint brace to assist or support a joint by increasing or decreasing resistance in the joint brace, or tension in the one or more tensioning elements.

Aspect 47: The joint brace of Aspect 45, wherein the one or more sensors are capable of measuring and monitoring an amount of tension present in the joint brace or the one or more tensioning elements, or the amount of unloading force applied at a wearer's joint.

Aspect 48: The joint brace of Aspect 45, wherein an amount of unloading force at a wearer's joint includes a variable amount that changes as the wearer's joint is extended or flexed.

Aspect 49: The joint brace of Aspect 45, wherein an analog value of tension applied at a wearer's joint is converted to a digital signal.

Aspect 50: The joint brace of Aspect 49, wherein the digital signal informs a wearer of the joint brace regarding how much tension is present in the joint brace or as a change in tension is recognized by the one or more sensors.

Aspect 51: The joint brace of Aspect 45, wherein the one or more sensors are fabricated on or within the brace.

Aspect 52: The joint brace of Aspect 45, wherein the one or more sensors output a digital or electronic signal, and wherein the one or more sensors connect to one or more lights or other indicator, including a viewing port, that indicate information about the joint brace, including an amount of force or tension in the joint brace.

Aspect 53: The joint brace of Aspect 45, further comprising a motor and control processor system, and further optionally comprising a potentiometer, gear box or gearing system, controller, pulley, or block and tackle system, or one or more servo arms or levers.

Aspect 54: The joint brace of Aspect 53, wherein the motor is operatively connected to the one or more tensioning element through a system of gears or screw(s), which are capable of gathering or releasing tension based on inputs from the one or more sensors, wherein the system is managed by a controller or processor.

Aspect 55: The joint brace of Aspect 45, wherein the one or more sensors are connected to a screen on the brace that communicates information such as force generated within the joint brace or weight unloaded by the joint brace.

Aspect 56: The joint brace of Aspect 45, wherein the one or more sensors are synced to a computer-implemented software application on an electronic device to provide a wearer with feedback about an amount of force being applied by the joint brace, a direction a wearer's joint is being overloaded in, or a direction in which a wearer's joint is being flexed or extended, and wherein data from the one or more sensors is analyzed to identify patterns, and is capable of being used as inputs to a controller that determines how one or more motors on the joint brace should function in an assistive or supportive manner.

Aspect 57: The unloading joint brace of Aspect 1, further comprising a tension, acceleration, position, and/or velocity measurement sensor or mechanism, wherein the measurements from the measurement sensor or mechanism are optionally converted to a digital signal and displayed as visual or audio output on the brace or an external electronic device.

Aspect 58: The unloading knee joint or elbow joint brace of Aspect 57, wherein the digital signal is used to activate one or more lights on the brace to indicate an amount of tension.

Aspect 59: The unloading knee joint or elbow joint brace of Aspect 57, wherein the digital signal is used to activate a visual indicator on the joint brace showing colors or lights to indicate an amount of tension on the one or more tensioning element to communicate to the wearer an amount of tension in the joint brace.

Aspect 60: The joint brace of Aspect 1, further comprising a motor and control processor system, and further optionally comprising a potentiometer, gear box or gearing system, or one or more servo arms or levers.

Aspect 61: The joint brace of Aspect 1, further comprising one or more motors and one or more sensors, wherein the one or more motors are operatively connected to the one or more tensioning element through a system of gears or screws capable of gathering or releasing tension based on inputs from the one or more sensors, wherein the system is managed by a controller or processor.

Aspect 62: The joint brace of Aspect 1, further comprising one or more motors and one or more sensors, wherein the one or more sensors are connected to a screen on the joint brace that communicates information such as force generated within the joint brace or weight unloaded by the joint brace to the wearer.

Aspect 63: The joint brace of Aspect 1, further comprising one or more motors and one or more sensors, wherein the one or more sensors are synced to a computer-implemented software application on an electronic device to provide the wearer with information about an amount of force being applied by the joint brace, a direction the joint is being overloaded in, or a direction in which the joint is being flexed or extended.

Aspect 64: The joint brace of Aspect 1, further comprising one or more motors and one or more sensors, wherein information from the one or more sensors is automatically analyzed to identify patterns and to send inputs to a controller to control the one or more motors, wherein the one or more motors function in an assistive or supportive manner to the wearer.

Aspect 65: The joint brace of Aspect 1, further comprising a tension, acceleration, position, and/or velocity measurement sensor or mechanism, wherein measurements from the measurement sensor or mechanism are optionally converted to a digital signal and displayed as visual or audio output on the joint brace or an external electronic device.

Aspect 66: The joint brace of Aspect 65, wherein the digital signal is used to activate one or more lights on the joint brace to indicate an amount of tension.

Aspect 67: The joint brace of Aspect 1, further comprising a visual indicator using different colors or lights to indicate different tension in the one or more tensioning element to communicate to the wearer an amount of tension in the joint brace.

Aspect 68: The joint brace of Aspect 1, further comprising one or more sensors, one or more processors, one or more controllers, one or more motors, or combinations thereof, wherein the one or more processors are located on the brace or on an external electronic device, including a computer, a computer processing unit, a laptop computer, a tablet computer, a phone, a smartphone, a server, internet, cloud, or combinations thereof.

Aspect 69: A joint brace, comprising:
an upper portion connected to an appendage above the joint and a lower portion connected to an appendage below the joint;
one or more tensioning elements;
an adjustable tensioning mechanism capable of adjusting tension in the one or more tensioning elements; and
one or more sensors, one or more processors, one or more motors, one or more controllers, or combinations thereof;
wherein the one or more sensors measure tension in the one or more tension elements and/or the joint brace;
wherein the one or more processors are located on the brace or on an external electronic device;
wherein the one or more sensors, one or more processors, one or more motors, one or more controllers, or combinations thereof, are capable of adjusting the adjustable tensioning mechanism and/or the one or more tensioning elements.

Aspect 70: The unloading joint brace of Aspect 69, wherein the one or more sensors are tension measurement sensors capable of being used to restrict a wearer from over-tensioning the one or more tensioning elements, or wherein the tension measurement sensors are capable of sending tension information and/or directly or indirectly controlling the adjustable tensioning mechanism.

Aspect 71: The unloading joint brace of Aspect 69, wherein the one or more sensors measure tension on the one or more tensioning elements, wherein the one or more sensors send tension data to the one or more processors, and wherein the one or more processors send instructions to the one or more controllers and/or the one or more motors.

Aspect 72: The unloading joint brace of Aspect 69, wherein the one or more processors are located on the joint brace or on an external electronic device in communication with the joint brace or the one or more sensors, including a computer, a computer processing unit, a laptop computer, a tablet computer, a phone, a smartphone, a server, internet, cloud, or combinations thereof.

Aspect 73: The unloading joint brace of Aspect 69, wherein the one or more controllers or one or more motors is capable of adjusting tension in the joint brace and/or the one or more tensioning elements, and wherein the adjustment is based on data from the one or more sensors.

Aspect 74: The unloading joint brace of Aspect 69, wherein the one or more sensors, one or more processors, one or more motors, one or more controllers, or combinations thereof, are capable of automatically adjusting tension in the joint brace and/or the one or more tensioning elements.

Aspect 75: The unloading joint brace of Aspect 69, wherein the one or more sensors, one or more processors, one or more motors, one or more controllers, or combinations thereof, are capable of automatically adjusting tension in the joint brace and/or one or more tensioning elements based on a preset upper and/or lower range of tension.

Aspect 76: The unloading joint brace of Aspect 69, wherein the one or more sensors, one or more processors, one or more motors, one or more controllers, or combinations thereof, are capable of providing feedback to a wearer about tension on the joint brace and/or motion of the joint.

Aspect 77: The unloading joint brace of claim 69, wherein the one or more sensors, one or more processors, one or more motors, one or more controllers, or combinations thereof, are capable of informing a wearer and/or another person that the joint brace and/or the one or more tensioning elements are overloaded.

Aspect 78: The unloading joint brace of Aspect 69, wherein the one or more sensors, one or more processors, one or more motors, one or more controllers, or combinations thereof, are capable of informing a wearer and/or another person information related to the joint brace, tension, the one or more tensioning elements, the hinge, a prescribed treatment, a joint movement, joint health, an injury, treatment options, or combinations thereof.

Aspect 79: The unloading joint brace of Aspect 69, wherein information about the joint brace or use of the joint brace is communicated to a wearer or another person, wherein performance or function of the joint brace is capable of being modified based on the information.

Aspect 80: A joint brace, wherein the joint brace is used for rehabilitation or physical therapy, wherein the joint brace generates electric impulses that stimulate muscles to contract to strengthen or repair tissue, including strengthening or repairing muscles which have become shortened, weakened, or atrophied due to injury or disease.

Aspect 81: The joint brace of claim 80, wherein the joint brace integrates electrical muscle stimulation (EMS or E-STIM therapy) equipment or electromyostimulation (EMS) or neuromuscular electrical stimulation (NMES) equipment that is attached to or integrated within the joint brace.

Aspect 82: A joint brace, wherein the joint brace is used for rehabilitation or physical therapy, wherein the joint brace generates electric impulses that use transcutaneous electrical nerve stimulation (TENS) to stimulate nerves for managing or blocking pain signals to a brain of a wearer, wherein a battery and electrodes are attached to or integrated within the joint brace.

Aspect 83: A joint brace or joint wrap, wherein the joint brace or joint wrap is used as a non-invasive mechanism for physical therapy or to rehabilitate joint or tissue, or to reduce pain in a wearer, wherein the joint brace or wrap is attached to or contains an apparatus that generates sound waves which cause vibrations that may be pulsed on and off or continuously.

Aspect 84: In aspects, the braces and orthotics described herein may be used in conjunction with sensors and/or motors.

Aspect 85: The brace or orthotic tension may be modified in real time or another time based on the user's needs.

Aspect 86: In aspects, the braces and orthotics described herein have the ability to communicate wirelessly, via Bluetooth, via WiFi, or via direct connection.

Aspect 87: In aspects, a user's knee is profiled and the injury is characterized to approximate how much assistive force should be applied as a function of degree of flexion. The need for support on either side of the tibiofemoral compartments is also considered and used as a design input.

Aspect 88: In Aspects, 3D scanning, radiographic data (e.g., x-rays, MRIs), patient reported pain levels, and measurements are used to design and/or adjust the brace and/or components of the brace.

Aspect 89: In aspects, computer-implemented software calculates and estimates relative portions of soft and firm tissue based on input such as 3D scans, user height, user weight, user BMI, user age, user-reported pain levels, and other historical information on the user.

Aspect 90: In aspects, computer-implemented software models the user's gait based on positioning data and determines the amount of corrective and assistive force to improve joint function and/or user health. In aspects, computer-implemented software estimates user's assistive and corrective needs for different activities and generates outputs for brace design parameters and/or tensioning or adjustments. In aspects, brace design may be partially or fully automated based on these design parameters.

Aspect 91: In aspects, extension and flexion stops are built into the brace design as a continuous material connected to the upper and lower brace portions.

Although the above-recited examples are not to be construed as limiting the scope of the various embodiments of the present disclosure, the examples indicate that the knee brace and hinge assemblies can be constructed for use in an elbow brace. It is apparent that the skilled artisan can modify the dimensions of the brace and hinge assemblies to treat pain and inflammation associated with a variety of elbow disorders. The same is true of the ankle and other joints.

It is also readily apparent that the range of adjustability of the braces within the scope of the present invention inter alia by selecting materials of different elasticity for construction of the arm members, by selecting different longitudinal or cross-sectional dimensions for the arm members, or by selecting pads of different fixed thicknesses or different ranges of adjustable thicknesses.

It is further evident that although the knee brace and hinge assemblies of the present invention have only been described above in terms of a few embodiments adapted to treat osteoarthritis, it is apparent to the skilled artisan that these embodiments are readily adaptable to treatment of pain associated with a variety of knee disorders. For example, additional embodiments envisioned with the scope of the present disclosure comprise hinge assemblies with the user tension adjustment handle, knob, etc. on the user's tibia versus the exemplified embodiment on the user's femur.

It is also apparent that the skilled artisan could easily modify the dimensions, materials, number and type of tensioning elements, and so forth to achieve an equivalent level of pain relief as the embodiments disclosed herein.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

The invention claimed is:

1. A joint brace comprising:
   a support comprising an upper portion and a lower portion;
   a center cap; and
   a polycentric hinge connected to the upper portion and the lower portion, the polycentric hinge having an upper hinge member comprising an upper pivot point and an upper articulating surface, and a lower hinge member comprising a lower pivot point and a lower articulating surface;
   wherein at least one of the upper articulating surface and the lower articulating surface are curved;
   wherein at least one side of the upper hinge member or the lower hinge member perpendicular or diagonal relative to the upper articulating surface or the lower articulating surface is curved;
   wherein one or more sides of the center cap are curved allowing for a curvature of the polycentric hinge to fully or partially conform to a shape of an anatomy of a user's joint or limb based on a joint measurement, a three-dimensional scan of the user's joint or limb, user measurements, user-reported information, a radiographic scan of the user's joint or limb, or a combination thereof.

2. The joint brace of claim 1, further comprising at least one tensioning element providing unloading or distracting forces, and wherein the upper portion and the lower portion with the at least one tensioning element provide a force to induce a joint separation or a joint distraction of the user's joint as a degree of flexion of the user's joint changes.

3. The joint brace of claim 1, wherein at least one of the upper hinge member and the lower hinge member comprise teethed gears, and wherein the teethed gears comprise variable radii providing joint distraction of the user's joint as a degree of flexion of the user's joint changes.

4. The joint brace of claim 1, wherein adjacent surfaces of the upper hinge member and the lower hinge member articulate relative to one another or against one another and have varying radii.

5. The joint brace of claim 1, wherein one or more pins connect the center cap to the upper hinge member and the lower hinge member, and wherein the center cap comprises slots allowing the upper hinge member and the lower hinge member to move apart with increasing radii, move closer together with decreasing radii, or combinations thereof.

6. The joint brace of claim 1, wherein the upper hinge member and the lower hinge member are connected by the center cap and one or more pins, and wherein a force is applied directly or indirectly to the one or more pins providing a counter-force between teethed gears, curved adjacent surfaces, or a combination thereof, of the polycentric hinge.

7. The joint brace of claim 1, wherein an amount of distracting force is capable of being tailored to a user and varies with a degree of flexion of the user's joint and optionally varies from one side of the user's joint to a second side of the user's joint.

8. The joint brace of claim 1, wherein the polycentric hinge comprises teethed gears or wherein the polycentric hinge comprises components that are capable of sliding with respect to one another.

9. The joint brace of claim 1, wherein the center cap is connected to the upper hinge member and the lower hinge member by one or more pins, wherein one or more of the upper hinge member, the lower hinge member, and the center cap are curved, and wherein the curvature of the upper hinge member, the lower hinge member, or the center cap are configured so that the upper hinge member, the lower hinge member, or the center cap are capable of rotating about one another or the one or more pins.

10. The joint brace of claim 1, further comprising a tensioning element, wherein the tensioning element is drawn over the polycentric hinge, wherein the tensioning element is integrated within the upper portion, the lower portion, or both, wherein the tensioning element is connected to a lace or wire drawn over the polycentric hinge, or combinations thereof.

11. The joint brace of claim 1, further comprising:
an adjustable tensioning element; and
one or more sensors, one or more processors, one or more motors, one or more controllers, or combinations thereof;
wherein the one or more sensors, one or more processors, one or more motors, one or more controllers, or combinations thereof, are capable of adjusting the adjustable tensioning element.

12. A brace for a joint comprising:
a support comprising an upper portion and a lower portion; and
a polycentric distracting hinge having two members, a first member attached to the upper portion having a first pivot point and a first articulating surface, and a second member attached to the lower portion having a second pivot point and a second articulating surface, wherein a radius between at least one of the first pivot point or the second pivot point and at least one of the first articulating surface or the second articulating surface increases as the two members articulate or move relative to one another or against one another, thereby providing a distraction force to push apart or pull apart the upper portion in a proximal direction and the lower portion in a distal direction;
wherein the polycentric distracting hinge is optionally curved or conformable to a user's anatomy; and
wherein the polycentric distracting hinge comprises teethed gears, curved adjacent surfaces, or a combination thereof.

13. The brace for a joint of claim 12, further comprising a tensioning element, wherein the tensioning element is located within either or both the upper portion and the lower portion.

14. The brace for a joint of claim 12, wherein the upper portion and the lower portion are connected by a center cap.

15. The brace for a joint of claim 12, wherein the upper portion and the lower portion are connected by a center cap and one or more pins, and wherein a force is applied directly or indirectly to the one or more pins providing a counterforce between the teethed gears, the curved adjacent surfaces, or a combination thereof, of the polycentric distracting hinge.

16. The brace for a joint of claim 12, wherein the upper portion and the lower portion are connected by a center cap, wherein the upper portion, the lower portion, the center cap, or combinations thereof, are curved to fully or partially conform to a user's joint or limb.

17. The brace for a joint of claim 12, wherein the polycentric distracting hinge, the upper portion, the lower portion, or combinations thereof, are shaped to a user's joint or limb based on a joint or limb measurement, three-dimensional scan of the user's joint or limb, or radiographic scan of the user's joint or limb.

18. The brace for a joint of claim 12, wherein an amount of the distracting force is capable of being tailored to the user based a three-dimensional scan, joint or limb measurements, user-reported information, radiographic information, or a combination thereof, and wherein the amount of the distraction force varies with degree of flexion of the user's joint and optionally varies from one side of the user's joint to a second side of the user's joint.

19. The brace for a joint of claim 12, wherein the upper portion and the lower portion are connected by a center cap, wherein the center cap is connected to the upper portion or the lower portion by one or more pins, wherein one or more of the upper portion, the lower portion, or the center cap are curved, and wherein the curvature of the upper portion, the lower portion, or the center cap are configured so that the upper portion, the lower portion, or the center cap are capable of rotating about one another or the one or more pins.

20. A joint brace comprising:
a support comprising an upper portion and a lower portion; and
a distracting hinge connected to the upper portion and the lower portion, wherein the distracting hinge is optionally curved or conformable to a user's anatomy;
wherein the distracting hinge comprises teethed gears, curved adjacent surfaces, or a combination thereof, wherein the teethed gears, curved adjacent surfaces, or a combination thereof comprise variable radii providing joint distraction upon articulating relative to one another or against one another;
wherein the variable radii is configured to increase or decrease a distance between the upper portion and the lower portion during joint articulation thereby providing a distraction force; and
wherein the upper portion and the lower portion are connected by a center cap, wherein the center cap supports a distraction force, and wherein an amount of the distraction force is capable of being tailored to a user based on a three-dimensional scan, joint or limb measurements, user-reported information, radiographic information, or a combination thereof, and wherein the amount of the distraction force may vary with degree of flexion of a user's joint and/or from one side of the user's joint to a second side of the user's joint.

21. A joint brace comprising:
a support comprising an upper portion and a lower portion; and
a pivoting hinge connected to the upper portion and the lower portion;
wherein the pivoting hinge is configured to allow for a curvature of the pivoting hinge to fully or partially conform to a shape of an anatomy of a user's joint or limb based on a joint measurement, a three-dimensional scan of the user's joint or limb, user measurements, user-reported information, a radiographic scan of the user's joint or limb, or a combination thereof; and
wherein the upper portion and the lower portion are connected by a center cap, wherein the center cap supports a distraction force, and wherein an amount of the distraction force is capable of being tailored to a user and varies with a degree of flexion of the user's joint and/or from one side of the user's joint to a second side of the user's joint.

* * * * *